(12) United States Patent
Bateman et al.

(10) Patent No.: US 8,232,107 B2
(45) Date of Patent: *Jul. 31, 2012

(54) METHODS FOR MEASURING THE METABOLISM OF NEURALLY DERIVED BIOMOLECULES IN VIVO

(75) Inventors: Randall John Bateman, Grover, MO (US); David Michael Holtzman, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/005,233

(22) Filed: Jan. 12, 2011

(65) Prior Publication Data

US 2011/0111511 A1    May 12, 2011

Related U.S. Application Data

(62) Division of application No. 11/910,463, filed as application No. PCT/US2006/012200 on Apr. 4, 2006, now Pat. No. 7,892,845.

(60) Provisional application No. 60/668,634, filed on Apr. 6, 2005.

(51) Int. Cl.
*B01D 59/44* (2006.01)
*G01N 33/58* (2006.01)
*G01N 33/68* (2006.01)
*G01N 33/487* (2006.01)

(52) U.S. Cl. .......................................... 436/86; 250/282

(58) Field of Classification Search ........................ None
See application file for complete search history.

(56) References Cited

U.S. PATENT DOCUMENTS

| | | | |
|---|---|---|---|
| 7,829,291 B2 * | 11/2010 | Caprioli | 435/7.1 |
| 2003/0228259 A1 | 12/2003 | Hellerstein | |
| 2005/0019251 A1 * | 1/2005 | Hellerstein | 424/1.11 |
| 2006/0020440 A1 | 1/2006 | Hellerstein | |
| 2009/0202432 A1 | 8/2009 | Schenk et al. | |

FOREIGN PATENT DOCUMENTS

| | | | |
|---|---|---|---|
| WO | 9917765 A1 | 4/1999 | |
| WO | 03061479 A1 | 7/2003 | |
| WO | 03068919 A2 | 8/2003 | |
| WO | 2004018997 A2 | 3/2004 | |
| WO | PCT/US2006/012200 | 4/2004 | |
| WO | 2005081943 A2 | 9/2005 | |
| WO | 2006107814 A2 | 10/2006 | |
| WO | 2009062152 A1 | 5/2009 | |

OTHER PUBLICATIONS

International Search Report dated Feb. 13, 2009 regarding PCT/US08/82985, 3 pages.
Bahmanyar, Localization of Amyloid B Protein Messenger RNA in Brains from Patients with Alzheimer's Disease, Science, Jul. 3, 1987, pp. 77-80, vol. 237.
Non-final Office action dated Mar. 31, 2010 from related U.S. Appl. No. 12/267,974, 12 pgs.
EP Search Report, regarding European Application No. EP06749116 dated Mar. 10, 2009, 3 pages.
Martin et al, Intracellular Accumulation of B-Amyloid in Cells Expressing the Swedish Mutant Amyloid Precursor Protein, J. Biol. Chem., 1995, pp. 26727-26730, vol. 270, No. 45.
Ando et al, Turnover of Myelin Lipids in Aging Brain*, Neurochemical Research, Jan. 2003, pp. 5-13, vol. 28, No. 1.
Nordin et al, Gradients of CSF Monoamine Metabolites: A Comparison Between Male and Female Volunteers, J. Psychiat..Res., 1995, pp. 133-140, vol. 29, No. 2.
Qiu et al, Degradation of Amyloid B-Protein by a Serine Protease-a2-Macroglobulin Complex, J.Biol.Chem., 1996, pp. 8443-8451, vol. 271, No. 14.
Savage et al, Turnover of Amyloid B-Protein in Mouse Brain and Acute Reduction of Its Level by Phorbol Ester, J. Neurosci., 1998, pp. 1743-1752, vol. 18, No. 5.
Jerzy et al, Total tau in cerebrospinal fluid differentiates Alzheimer's disease from vascular dementia, Medical Science Monitor: International Medical Journal of Experimental and Clinical Research, Nov. 2003, pp. CR484-8, vol. 9, No. 11 (Abstract Only).
Yarasheski, et al, Increased plasma Gln and Leu Ra and inappropriately low muscle protein synthesis rate in AIDS wasting, Am Physiol Soc, 1998, pp. E577-E583, vol. 275.
International Search Report dated Aug. 1, 2008 regarding PCT/USO6/12200, 7 pages.
Yarasheski, Managing Sarcopenia With Progressive Resistance Exercise Training, J Nutr Health & Aging, 2002, pp. 1-8, vol. 6, No. 5.
Non-Final Rejection dated Dec. 30, 2008 from related U.S. Appl. No. 11/910,463.
Final Rejection dated Feb. 23, 2010 from related U.S. Appl. No. 11/910,463.
Bateman, at al, Stable Isotope Labeling Tandem Mass Spectrometry (SILT) to Quantify Protein Production and Clearance Rates, J Am Soc Mass Spectrom, 2007. pp. 997-1006, vol. 18.
Bateman, et al, Human amyloid-β synthesis and clearance rates as measured in cerebrospinal fluid in vivo, Nature Medicine, 2006, pp. 856-861, vol. 12, No. 7.
Berg, et al, Clinicopathologic Studies in Cognitively Healthy Aging and Alzheimer Disease, Arch Neurol, 1998, pp. 326-334, vol. 55.
Cirrito, et al, In Vivo Assessment of Brain Interstitial Fluid with Microdialysis Reveals Plaque-Associated Changes in Amyloid-β Metabolism and Half-Life, J of Neuroscience, 2003, pp. 8844-8853, vol. 23, No. 26.
Corder, et al, Gene Dose of Apolipoprotein E Type 4 Allele and the Risk of Alzheimer's Disease in Late Onset Families, Science, 1993, pp. 921-923, vol. 261.

(Continued)

*Primary Examiner* — Jeffrey Stucker
*Assistant Examiner* — Stephen Gucker
(74) *Attorney, Agent, or Firm* — Polsinelli Shughart PC

(57) ABSTRACT

The present invention relates to methods of diagnosing, monitoring, and assessing treatment effects for neurological and neurodegenerative diseases and disorders, such as Alzheimer's Disease, early in the course of clinical disease or prior to the onset of brain damage and clinical symptoms. Methods of measuring the in vivo metabolism of biomolecules produced in the CNS in a subject are provided.

13 Claims, 24 Drawing Sheets

OTHER PUBLICATIONS

Corder, et al, No Increased Risk of the Apolipoprotein E ε2 Allele with Early-Onset Alzheimer's Disease, Annals of Neurology, 1996, pp. 373-374, vol. 39, No. 3.

Corder, et al, The Apolipoprotein E E4 Allele and Sex-Specic Risk of Alzheimer'Disease, JAMA, 1995, pp. 373-374, vol. 273, No. 5.

Cutler, et al, Dose-dependent CSF acetylcholinesterase inhibition by SDZ ENA 713 in Alzheimer's disease, Acta Neurol Scand, 1998, pp. 244-250, vol. 97.

DeMattos, et al, ApoE and Clusterin Cooperatively Suppress Aβ Levels and Deposition: Evidence that ApoE Regulates Extracellular Aβ Metabolism in Vivo, Neuron, 2004, pp. 193-202, vol. 41.

DeMattos, et al, Peripheral anti-Aβ antibody alters CNS and plasma Aβclearance and decreases brain Aβ burden in a mouse model of Alzheimer's disease, PNAS, 2001, pp. 8850-8855, vol. 98, No. 15.

Elias; et al, In Vivo Metabolism of ApoB, ApoA-I, and VLDL Triglycerides in a Form of Hypobetalipoproteinemia Not Linked to the ApoB Gene, Arterioscler Thromb Vasc Biol, 2000, pp. 1309-1315, vol. 20.

Fagan, et al, Human and Murine ApoE Markedly Alters Aβ Metabolism before and after Plaque Formation in Mouse Model of Alzheimer's Disease, Neurobiology of Disease, 2002, pp. 305-318, vol. 9.

Fryer, et al, Human Apolipoprotein E4 Alters the Amyloid-β 40:42 Ratio and Promotes the Formation of Cerebral Amyloid Angiopathy in an Amyloid Precursor Protein Transgenic Model, J Neurosci, 2005, pp. 2803-2810, vol. 25, No. 11.

Games, et al, Alzhemer-type neuropathology in transgenic mice overexpressing V717F β-amyloid precursor protein, Nature, 1995, pp. 523-527, vol. 373.

Gersovitz, et al, Albumin Synthesis in Young and Elderly Subjects Using a New Stable Isotope Methodology: Response to Level of Protein Intake, Metabolism, 1980, pp. 1075-1086, vol. 29, No. 11.

Grundy, et al, Kinetic Mechanisms Determining Variability in Low Density Lipoprotein Levels and Rise with Age, Arteriosclerosis, 1985, pp. 623-630, vol. 5.

Haas, et al, Evidence of a Source of HIV Type 1 within the Central Nervous System by Ultraintensive Sampling of Cerebrospinal Fluid and Plasma, Aids Research & Human Retroviruses, 2000, pp. 1491-1502, vol. 16, No. 15.

Haas, et al, Two phases of HIV RNA decay in CSF during initial days of multidrug therapy, Neurology, 2003, pp. 1391-1396, vol. 61.

Hasten, et al, Isolation of human skeletal muscle myosin heavy chain and actin for measurement of fractional synthesis rates, American Physiological Society, 1998, pp. E1092-E1099, vol. 275.

Hasten, et al, Resistance exercise acutely increases MHC and mixed muscle protein synthesis rates in 78-84 and 23-32 yr olds, Am J Physiol Endocrinol Metab, 2000, pp. E620-E626, vol. 278.

Herbert, et al, Annual Incidence of Alzheimer Disease in the United States Projected to the Years 2000 through 2050, Alzheimer Disease and Associated Disorders, 2001, pp. 169-173, vol. 15, No. 4.

Holtzman, et al, Acid Urea Polyacrylamide Gel Electrophoresis: A Completely Denaturing Protocol for the Identification of Multiple Aβ Peptides Within a Single Lane, Society for Neuroscience Abstract, 2002.

Holtzman, et al, Apolipoprotein E Facilitates Neuritic and Cerebrovascular Plaque Formation in an Alzheimer's Disease Model, Ann. Neurol., 2000, pp. 739-747, vol. 47.

Holtzman, et al, Apolipoprotein E isoform-dependent amyloid deposition and neuritic degeneration in a mouse model of Alzheimer's disease, PNAS, 2000, pp. 2892-2897, vol. 97, No. 6.

Houle, et al, Pump-regulated Lumbar Subarachnoid Drainage, Neurosurgery, 2000, pp. 929-932, vol. 46, No. 4.

Kennedy, et al, Preferential Cerebrospinal Fluid Acetylcholinesterase Inhibition by Rivastigmine in Humans, J. Clin Psychopharmacol, 1999, pp. 513-521, vol. 19, No. 6.

Klunk, et al, Imaging Brain Amyloid in Alzheimer's Disease with Pittsburgh Compound-B, Ann Neural, 2804, pp. 306-319, vol. 55.

Kukull, et al, Dementia and Alzheimer Disease Incidence, Arch Neurol, 2002, pp. 1737-1746, vol. 59.

Kuo, et al, Water-soluble Aβ (N-40, N-42) Oligomers in Normal and Alzheimer Disease Brains, J Biol Chem, 1996, pp. 4077-4081, vol. 271, No. 8.

Lanz, et al, Studies of Aβ Pharmacodynamics in the Brain, Cerebrospinal Fluid, and Plasma in Young (Plaque-Free) Tg2576 Mice Using the γ-Secretase Inhibitor N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninarnide (LY-411575), J Pharmacol Exp Ther, 2004, pp. 49-55, vol. 309, No. 1.

Mayeux, et al, The Apolipoprotein ε4 Allele in Patients with Alzheimer's Disease, Ann Neural, 1993, pp. 752-754, vol. 34.

Merchak, et al, Use of Stable isotope labeling technique and mass isotopomer distribution analysis of [13C]palmitate isolated from surfactant disaturated phospholipids to study surfactant in vivo kinetics in a premature infant, J Mass Spectrom, 2000, pp. 734-738, vol. 35.

Morris, et al, Mild Cognitive Impairment Represents Early-Stage Alzheimer Disease, Arch Neurol, 2001, pp. 397-405, vol. 58.

Morris, et al, Pathologic Correlates of Nondemented Aging, Mild Cognitive Impairment, and Early-Stage Alzheimer's Disease, J Mol Neuro, 2001, pp. 101-118, vol. 17.

Murphy, et al, Presenilin 1 Regulates Pharmacologically Distinct γ-Secretase Activities, J Biol Chem, 2000, pp. 26277-26284, vol. 275, No. 34.

Patterson, Use of Stable Isotopically Labeled Tracers for Studies of Metabolic Kinetics: An Overview, Metabolism, 1997, pp. 322-329, vol. 46, No. 3.

Patterson, et al, Use of stable isotopically labeles tracers to measure very low density lipoprotein-triglyceride turnover, J. of Lipid Research, 2002, pp. 223-233, vol. 43.

Pinto, et al, Plasma Kinetics of a Cholesterol-Rich Emulsion in Young, Middle-Aged, and Elderly Subjects, Lipids, 2001, pp. 1307-1311, vol. 36, No. 12.

Pitas, et al, Astrocytes synthesize apolipoprotein E and metabolize apolipoprotein E-Containing lipoproteins. Biochim Biophys Acta, 1987, pp. 148-161, vol. 917.

Price, et al, Neuron Number in the Entorhinal Cortex and CA1 in Preclinical Alzheimer Disease, Arch Neurol, 2001, pp. 1395-1402, vol. 58.

Schulte, et al, Effects of Resistancee Training on the Rate of Muscle Protein Synthesis in Frail Elderly People. IntJ Sport Nutr Exerc Metab, 2001, pp. S111-S118, vol. 11.

Shibata, et al, Clearance of Alzheimer's amyloid-β1-40 peptide from brain by LDL receptor-related protein-1 at the blood-brain barrier, J. Clin Invest, 2000, pp. 1489-1499, vol. 106, No. 12.

Smith, et al, Kinetics of Neutral Amino Acid Transport Across the Blood-Brain Barrier, J. of Neurochem, 1987, pp. 1651-1658, vol. 49.

Talbot, et al, Protection against Alzheimer's disease with apoE ε2, Lancet, 1994, pp. 1432-1433, vol. 343.

Wang, et al, The Profile of Solube Amyloid β Protein in Cultured Cell Media, J Biol Chem, 1996, pp. 31894-31902, vol. 271, No. 50.

Williams, Spinal catheter insertion via seated lumbar puncture using a message chair, Neurology, 2002, pp. 1859-1860, vol. 58.

Wisniewski, et al, Occurrence of Neuropathological Changes and Dementia of Alzheimer's Disease in Down's Syndrome, Ann Neurol, 1985, pp. 278-282, vol. 17.

Yarasheski, et al, Reducing plasma HIV RNA improves muscle amino acid metabolism, Am J Physiol. Endocrinol. Metab, 2005, pp. E278-E284, vol. 288.

Yarasheski, et al, Measurement of Muscle Protein Fractional Synthetic Rate by Capillary Gas Chromatography/Combustion Isotope Ratio Mass Spectrometry, Biol Mass Spectrum, 1992, pp. 486-490, vol. 21.

Yarasheski, Exercise, Aging, and Muscle Protein Metabolism, J. Gerontol A Biol Sci Med Sci, 2003, pp. 918-922, vol. 58A, No. 10.

International Search Report and Written Opinion from related application, PCT/US09/64146, dated Jan. 13, 2010, 8 pgs.

Kar et al., "Interactions between β-amyloid and central cholinergic neurons: implications for Alzheimer's disease", J Psychiatry Neurosci, 2004; pp. 427-441; vol. 29, No. 6.

Final Office action dated Sep. 24, 2010 from related U.S. Appl. No. 12/267,974, 12 pgs.

Olsson et al, "Measurement of a- and B-secretase cleaved amyloid precursor protein in cerebrospinal fluid from Alzheimer patients", Experimental Neurology, 2003, 183:74-80.

English translation of Japanese language office action from related JP Application No. 2008-505406, mailing date May 24, 2011, 3 pgs.

Office action dated Feb 3, 2012 from related application EP 06 749 116.7.

Office Action dated Apr. 4, 2012 for related U.S. Appl. No. 13/129,036, 12 pages.

Office Action dated Apr. 1, 2012 from related Chinese Patent Application No. 200680019537.6, English translation only, 6 pages.

* cited by examiner

SEQUENCE LISTING

<160> NUMBER OF SEQ ID NOS: 3

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 12
<212> TYPE: PRT
<213> ORGANISM: Homo sapiens

<400> SEQUENCE: 2

Leu Val Phe Phe Ala Glu Asp Val Gly Ser Asn Lys
1               5                   10

<210> SEQ ID NO 3
<211> LENGTH: 12
<212> TYPE: PRT
<213> ORGANISM: Homo sapiens

<400> SEQUENCE: 3

Ser Trp Phe Glu Pro Leu Val Glu Asp Met Gln Arg
1               5                   10

METHODS FOR MEASURING THE METABOLISM OF NEURALLY DERIVED BIOMOLECULES IN VIVO

CROSS REFERENCE TO RELATED APPLICATIONS

This application is a divisional of U.S. application Ser. No. 11/910,463, filed Oct. 19, 2007, now U.S. Pat. No. 7,892,845 which is a US National of PCT Application PCT/US2006/012200, filed Apr. 4, 2006, which claims the priority of U.S. provisional application No. 60/668,634, filed Apr. 6, 2005, each of which is hereby incorporated by reference in its entirety.

ACKNOWLEDGEMENT OF FEDERAL RESEARCH SUPPORT

The present invention was made, at least in part, with government support under grants P50-AG05681, M01 RR00036, RR000954, and DK056341 awarded by the National Institutes of Health. Accordingly, the United States Government has certain rights in this invention.

FIELD OF THE INVENTION

The invention relates to methods for the diagnosis and treatment of neurological and neurodegenerative diseases, disorders, and associated processes. The invention also relates to a method for measuring the metabolism of central nervous system derived biomolecules in a subject in vivo.

BACKGROUND OF INVENTION

Alzheimer's Disease

Alzheimer's Disease (AD) is the most common cause of dementia and is an increasing public health problem. It is currently estimated to afflict 5 million people in the United States, with an expected increase to 13 million by the year 2050 (Herbert et al 2001, Alzheimer Dis. Assoc. Disord. 15(4): 169-173). AD, like other central nervous system (CNS) degenerative diseases, is characterized by disturbances in protein production, accumulation, and clearance. In AD, dysregulation in the metabolism of the protein, amyloid-beta (Aβ), is indicated by a massive buildup of this protein in the brains of those with the disease. AD leads to loss of memory, cognitive function, and ultimately independence. It takes a heavy personal and financial toll on the patient and the family. Because of the severity and increasing prevalence of this disease in the population, it is urgent that better treatments be developed.

Currently, there are some medications that modify symptoms, however, there are no disease-modifying treatments. Disease-modifying treatments will likely be most effective when given before the onset of permanent brain damage. However, by the time clinical diagnosis of AD is made, extensive neuronal loss has already occurred (Price et al. 2001, Arch. Neurol. 58(9): 1395-1402). Therefore, a way to identify those at risk of developing AD would be most helpful in preventing or delaying the onset of AD. Currently, there are no means of identifying the pathophysiologic changes that occur in AD before the onset of clinical symptoms or of effectively measuring the effects of treatments that may prevent the onset or slow the progression of the disease.

A need exists, therefore, for a sensitive, accurate, and reproducible method for measuring the in vivo metabolism of biomolecules in the CNS. In particular, a method is needed for measuring the in vivo fractional synthesis rate and clearance rate of proteins associated with a neurodegenerative disease, e.g., the metabolism of Aβ in AD.

SUMMARY OF INVENTION

An aspect of the current invention is the provision of means for diagnosing and monitoring the advent and progress of neurological and neurodegenerative diseases, such as AD, prior to the onset of brain damage and clinical symptoms. Another aspect of the invention provides means for monitoring the effects of the treatment of neurological and neurodegenerative diseases, such as AD.

A further aspect of the invention provides methods for measuring the in vivo metabolism (e.g., the rate of synthesis, the rate of clearance) of neurally derived biomolecules.

An additional aspect of the invention encompasses kits for measuring the in vivo metabolism of neurally derived proteins in a subject, whereby the metabolism of the protein may be used as a predictor of a neurological or a neurodegenerative disease, an monitor of the progression of the disease, or an indicator in the effectiveness of a treatment for the disease.

Other aspects and iterations of the invention are described in more detail herein.

DETAILED DESCRIPTION OF THE PREFERRED EMBODIMENTS

Figure 1:
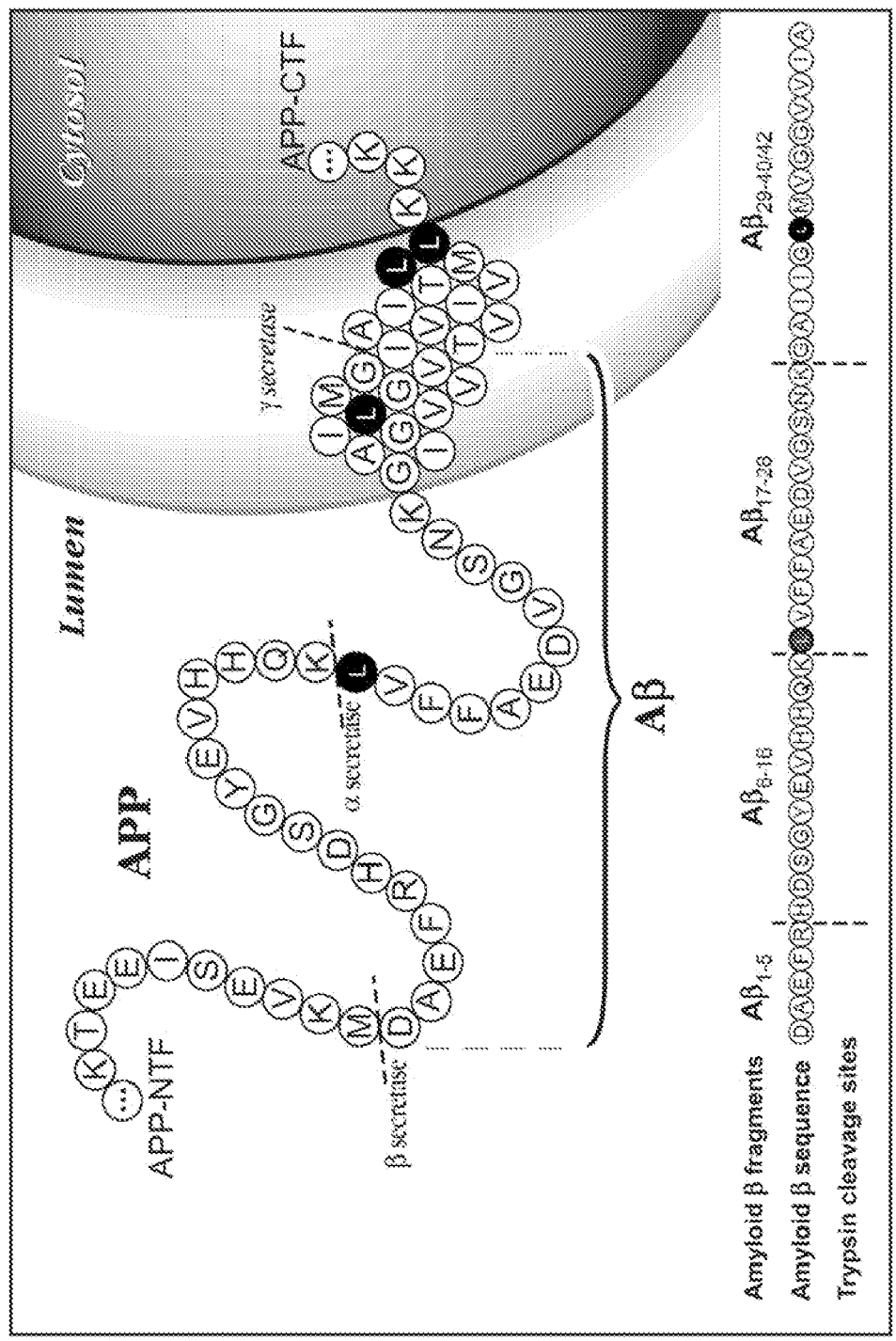
FIG. 1 depicts a schematic illustrating the processing of amyloid precursor protein (APP) into amyloid-β (Aβ) within a cell. Leucines (L), one of the possible labeling sites, are indicated in black. The amino acid sequence of Aβ (SEQ ID NO:1) is shown at the bottom, with the trypsin digest sites indicated to demonstrate the fragments that were analyzed by mass spectrometry.

The present invention relates to methods for the early diagnosis, prognosis, and assessment of treatment effectiveness of neurological and neurodegenerative diseases, disorders, and processes in a subject. Specifically, the invention provides a method for diagnosis prior to and after the onset of clinical symptoms associated with neural damage by determining the synthesis and clearance rates of CNS derived biomolecules. It also provides a method to assess whether a treatment is affecting the production or clearance rate of biomolecules in the CNS relevant to neurological and neurodegenerative diseases. The usefulness of this invention will be evident to those of skill in the art in that early diagnosis provides the opportunity for early treatment and, possibly, the prevention of significant neural damage in those afflicted. This invention provides a method for monitoring the effectiveness of disease-modifying therapies or for the screening of therapies likely to have a significant effect directly in humans. For example, one may determine if a treatment alters the synthesis or clearance rate of a biomolecule derived from the CNS. Ultimately, this method may provide a predictive test for the advent of neurological and neurodegenerative diseases, provide a method for more accurate diagnosis, and a means to monitor the progression of such diseases.

I. Methods for Monitoring the In Vivo Metabolism of Neurally Derived Biomolecules The current invention provides methods for measuring the in vivo metabolism of neurally derived biomolecules. By using this method, one skilled in the art may be able to study possible changes in the metabolism (synthesis and clearance) of a relevant neurally derived biomolecule implicated in a particular disease state. In addition, the invention permits the measurement of the pharmacodynamic effects of disease-modifying therapeutics in a subject.

In particular, this invention provides a method to label a biomolecule as it is synthesized in the central nervous system in vivo; to collect a biological sample containing labeled and unlabeled biomolecules; and a means to measure the labeling of the biomolecule over time. These measurements may be used to calculate metabolic parameters, such as the synthesis and clearance rates within the CNS, as well as others.

(a) Degenerative Diseases

Alzheimer's Disease (AD) is a debilitating disease characterized by accumulation of amyloid plaques in the central nervous system (CNS) resulting from increased production, decreased clearance, or both of amyloid-β (Aβ) protein. The inventors have developed a method for measuring the in vivo metabolism of Aβ in a human by measuring the in vivo synthesis and clearance rates of Aβ in the cerebrospinal fluid (CSF) or plasma. The in vivo synthesis and clearance rates of Aβ then may be used to assess whether a subject has an alteration in Aβ synthesis or clearance as compared to a control group. Such a comparison may allow for the diagnosis of AD early in its course, i.e., prior to the onset of clinical symptoms and significant neural damage. In addition, the present invention provides means to determine whether apolipoprotein E (ApoE) causes a change in Aβ metabolism. This determination may provide new insights about why particular ApoE genotypes are a risk factor for AD.

Those of skill in the art will appreciate that, while AD is the exemplary disease that may be diagnosed or monitored by the invention, the invention is not limited to AD. It is envisioned that the method of the invention may be used in the diagnosis and assessment of treatment efficacy of several neurological and neurodegenerative diseases, disorders, or processes including, but not limited to, Parkinson's Disease, stroke, frontal temporal dementias (FTDs), Huntington's Disease, progressive supranuclear palsy (PSP), corticobasal degeneration (CBD), aging-related disorders and dementias, Multiple Sclerosis, Prion Diseases (e.g. Creutzfeldt-Jakob Disease, bovine spongiform encephalopathy or Mad Cow Disease, and scrapie), Lewy Body Disease, and Amyotrophic Lateral Sclerosis (ALS or Lou Gehrig's Disease). It is also envisioned that the method of the invention may be used to study the normal physiology, metabolism, and function of the CNS.

Neurological and neurodegenerative diseases are most common in subjects of advanced age. For example, 10% of people over the age of 65 have AD, while about 50% of people over age 85 are afflicted with AD. Because of the prevalence of neurological and neurodegenerative diseases among the aging human population and the health care costs associated with these diseases, it is envisioned that the in vivo metabolism of biomolecules will be measured in a human subject, and in particular, in a human subject with advanced age. Alternatively, the in vivo metabolism of biomolecules may be measured in other mammalian subjects. In another embodiment, the subject is a companion animal such as a dog or cat. In another alternative embodiment, the subject is a livestock animal such as a cow, pig, horse, sheep or goat. In yet another alternative embodiment, the subject is a zoo animal. In another embodiment, the subject is a research animal such as a non-human primate or a rodent.

(b) Biomolecule

The present invention provides a method for measuring the metabolism of a biomolecule derived from the CNS in vivo. The biomolecule may be a protein, a lipid, a nucleic acid, or a carbohydrate. The possible biomolecules are only limited by the ability to label them during in vivo synthesis and collect a sample from which their metabolism may be measured. In a preferred embodiment, the biomolecule is a protein synthesized in the CNS. For example, the protein to be measured may be, but is not limited to, amyloid-β (Aβ) and its variants, soluble amyloid precursor protein (APP), apolipoprotein E (isoforms 2, 3, or 4), apolipoprotein J (also called clusterin), Tau (another protein associated with AD), glial fibrillary acidic protein, alpha-2 macroglobulin, synuclein, S100B, Myelin Basic Protein (implicated in multiple sclerosis), prions, interleukins, TDP-43, superoxide dismutase-1, huntingtin, and tumor necrosis factor (TNF). Additional biomolecules that may be targeted include products of, or proteins or peptides that interact with GABAergic neurons, noradrenergic neurons, histaminergic neurons, seratonergic neurons, dopaminergic neurons, cholinergic neurons, and glutaminergic neurons.

In an exemplary embodiment, the protein whose in vivo metabolism is measured may be amyloid-beta (Aβ) protein. In a further embodiment, other variants of Aβ (e.g., 40, 42, 38 or others) may be measured. In yet a further embodiment, digestion products of Aβ (e.g., $A\beta_{6-16}$, $A\beta_{17-28}$) may be measured.

(c) Labeled Moiety

Several different moieties may be used to label the biomolecule of interest. Generally speaking, the two types of labeling moieties typically utilized in the method of the invention are radioactive isotopes and non-radioactive (stable) isotopes. In a preferred embodiment, non-radioactive isotopes may be used and measured by mass spectrometry. Preferred stable isotopes include deuterium $^2H$, $^{13}C$, $^{15}N$, $^{17}$ or $^{18}O$ $^{33, 34,}$ or $^{36}S$, but it is recognized that a number of other stable isotope that change the mass of an atom by more or less neutrons than is seen in the prevalent native form would also be effective. A suitable label generally will change the mass of the biomolecule under study such that it can be detected in a mass spectrometer. In one embodiment, the biomolecule to be measured is a protein, and the labeled moiety is an amino acid comprising a non-radioactive isotope (e.g., $^{13}C$). In another embodiment, the biomolecule to be measured is a nucleic acid, and the labeled moiety is a nucleoside triphosphate comprising a non-radioactive isotope (e.g., $^{15}N$). Alternatively, a radioactive isotope may be used, and the labeled biomolecules may be measured with a scintillation counter rather than a mass spectrometer. One or more labeled moieties may be used simultaneously or in sequence.

In a preferred embodiment, when the method is employed to measure the metabolism of a protein, the labeled moiety typically will be an amino acid. Those of skill in the art will appreciate that several amino acids may be used to provide the label of a biomolecule. Generally, the choice of amino acid is based on a variety of factors such as: (1) The amino acid generally is present in at least one residue of the protein or peptide of interest. (2) The amino acid is generally able to quickly reach the site of protein synthesis and rapidly equilibrate across the blood-brain barrier. Leucine is a preferred amino acid to label proteins that are synthesized in the CNS, as demonstrated in Examples 1 and 2. (3) The amino acid ideally may be an essential amino acid (not produced by the body), so that a higher percent of labeling may be achieved. Non-essential amino acids may also be used; however, measurements will likely be less accurate. (4) The amino acid label generally does not influence the metabolism of the protein of interest (e.g., very large doses of leucine may affect muscle metabolism). And (5) availability of the desired amino acid (i.e., some amino acids are much more expensive or harder to manufacture than others). In one embodiment, $^{13}C_6$-phenylalanine, which contains six $^{13}C$ atoms, is used to label a neurally derived protein. In a preferred embodiment, $^{13}C_6$-leucine is used to label a neurally derived protein. In an exemplary embodiment, $^{13}C_6$-leucine is used to label amyloid-β.

There are numerous commercial sources of labeled amino acids, both non-radioactive isotopes and radioactive isotopes. Generally, the labeled amino acids may be produced either biologically or synthetically. Biologically produced amino acids may be obtained from an organism (e.g., kelp/seaweed) grown in an enriched mixture of $^{13}C$, $^{15}N$, or another isotope that is incorporated into amino acids as the organism produces proteins. The amino acids are then separated and purified. Alternatively, amino acids may be made with known synthetic chemical processes.

(d) Administration of the Labeled Moiety

The labeled moiety may be administered to a subject by several methods. Suitable methods of administration include intravenously, intra-arterially, subcutaneously, intraperitoneally, intramuscularly, or orally. In a preferred embodiment, the labeled moiety is a labeled amino acid, and the labeled amino acid is administered by intravenous infusion. In another embodiment, labeled amino acids may be orally ingested.

The labeled moiety may be administered slowly over a period of time or as a large single dose depending upon the type of analysis chosen (e.g., steady state or bolus/chase). To achieve steady-state levels of the labeled biomolecule, the labeling time generally should be of sufficient duration so that the labeled biomolecule may be reliably quantified. In one embodiment, the labeled moiety is labeled leucine and the labeled leucine is administered intravenously for nine hours. In another embodiment, the labeled leucine is administered intravenously for 12 hours.

Those of skill in the art will appreciate that the amount (or dose) of the labeled moiety can and will vary. Generally, the amount is dependent on (and estimated by) the following factors. (1) The type of analysis desired. For example, to achieve a steady state of about 15% labeled leucine in plasma requires about 2 mg/kg/hr over 9 hr after an initial bolus of 2 mg/kg over 10 min. In contrast, if no steady state is required, a large bolus of labeled leucine (e.g., 1 or 5 grams of labeled leucine) may be given initially. (2) The protein under analysis. For example, if the protein is being produced rapidly, then less labeling time may be needed and less label may be needed—perhaps as little as 0.5 mg/kg over 1 hour. However, most proteins have half-lives of hours to days and, so more likely, a continuous infusion for 4, 9 or 12 hours may be used at 0.5 mg/kg to 4 mg/kg. And (3) the sensitivity of detection of the label. For example, as the sensitivity of label detection increases, the amount of label that is needed may decrease.

Those of skill in the art will appreciate that more than one label may be used in a single subject. This would allow multiple labeling of the same biomolecule and may provide information on the production or clearance of that biomolecule at different times. For example, a first label may be given to subject over an initial time period, followed by a pharmacologic agent (drug), and then a second label may be administered. In general, analysis of the samples obtained from this subject would provide a measurement of metabolism before AND after drug administration, directly measuring the pharmacodynamic effect of the drug in the same subject.

Alternatively, multiple labels may be used at the same time to increase labeling of the biomolecule, as well as obtain labeling of a broader range of biomolecules.

(e) Biological Sample

The method of the invention provides that a biological sample be obtained from a subject so that the in vivo metabolism of the labeled biomolecule may be determined. Suitable biological samples include, but are not limited to, cerebral spinal fluid (CSF), blood plasma, blood serum, urine, saliva, perspiration, and tears. In one embodiment of the invention, biological samples are taken from the CSF. In an alternate embodiment, biological samples are collected from the urine. In a preferred embodiment, biological samples are collected from the blood.

Cerebrospinal fluid may be obtained by lumbar puncture with or without an indwelling CSF catheter (a catheter is preferred if multiple collections are made over time). Blood may be collected by veni-puncture with or without an intravenous catheter. Urine may be collected by simple urine collection or more accurately with a catheter. Saliva and tears may be collected by direct collection using standard good manufacturing practice (GMP) methods.

In general when the biomolecule under study is a protein, the invention provides that a first biological sample be taken from the subject prior to administration of the label to provide a baseline for the subject. After administration of the labeled amino acid or protein, one or more samples generally would be taken from the subject. As will be appreciated by those of skill in the art, the number of samples and when they would be taken generally will depend upon a number of factors such as: the type of analysis, type of administration, the protein of interest, the rate of metabolism, the type of detection, etc.

In one embodiment, the biomolecule is a protein and samples of blood and CSF are taken hourly for 36 hours. Alternatively, samples may be taken every other hour or even less frequently. In general, biological samples obtained during the first 12 hours of sampling (i.e., 12 hrs after the start of labeling) may be used to determine the rate of synthesis of the protein, and biological samples taken during the final 12 hours of sampling (i.e., 24-36 hrs after the start of labeling) may be used to determine the clearance rate of the protein. In another alternative, one sample may be taken after labeling for a period of time, such as 12 hours, to estimate the synthesis rate, but this may be less accurate than multiple samples. In yet a further alternative, samples may be taken from an hour to days or even weeks apart depending upon the protein's synthesis and clearance rate.

(f) Detection

The present invention provides that detection of the amount of labeled biomolecule and the amount of unlabeled biomolecule in the biological samples may be used to determine the ratio of labeled biomolecule to unlabeled biomolecule. Generally, the ratio of labeled to unlabeled biomolecule is directly proportional to the metabolism of the biomolecule. Suitable methods for the detection of labeled and unlabeled biomolecules can and will vary according to the biomolecule under study and the type of labeled moiety used to label it. If the biomolecule of interest is a protein and the labeled moiety is a non-radioactively labeled amino acid, then the method of detection typically should be sensitive enough to detect changes in mass of the labeled protein with respect to the unlabeled protein. In a preferred embodiment, mass spectrometry is used to detect differences in mass between the labeled and unlabeled proteins. In one embodiment, gas chromatography mass spectrometry is used. In an alternate embodiment, MALDI-TOF mass spectrometry is used. In a preferred embodiment, high-resolution tandem mass spectrometry is used.

Additional techniques may be utilized to separate the protein of interest from other proteins and biomolecules in the biological sample. As an example, immunoprecipitation may be used to isolate and purify the protein of interest before it is analyzed by mass spectrometry. Alternatively, mass spectrometers having chromatography setups may be used to isolate proteins without immunoprecipitation, and then the protein of interest may be measured directly. In an exemplary embodiment, the protein of interest is immunoprecipitated and then analyzed by a liquid chromatography system interfaced with a tandem MS unit equipped with an electrospray ionization source (LC-ESI-tandem MS).

The invention also provides that multiple proteins or peptides in the same biological sample may be measured simultaneously. That is, both the amount of unlabeled and labeled protein (and/or peptide) may be detected and measured separately or at the same time for multiple proteins. As such, the invention provides a useful method for screening changes in synthesis and clearance of proteins on a large scale (i.e. proteomics/metabolomics) and provides a sensitive means to detect and measure proteins involved in the underlying pathophysiology. Alternatively, the invention also provides a means to measure multiple types of biomolecules. In this context, for example, a protein and a carbohydrate may be measured simultaneously or sequentially.

(g) Metabolism Analysis

Once the amount of labeled and unlabeled biomolecule has been detected in a biological sample, the ratio or percent of labeled biomolecule may be determined. If the biomolecule of interest is a protein and the amount of labeled and unlabeled protein has been measured in a biological sample, then the ratio of labeled to unlabeled protein may be calculated. Protein metabolism (synthesis rate, clearance rate, lag time, half-life, etc.) may be calculated from the ratio of labeled to unlabeled protein over time. There are many suitable ways to calculate these parameters. The invention allows measurement of the labeled and unlabeled protein (or peptide) at the same time, so that the ratio of labeled to unlabeled protein, as well as other calculations, may be made. Those of skill in the art will be familiar with the first order kinetic models of labeling that may be used with the method of the invention. For example, the fractional synthesis rate (FSR) may be calculated. The FSR equals the initial rate of increase of labeled to unlabeled protein divided by the precursor enrichment. Likewise, the fractional clearance rate (FCR) may be calculated. In addition, other parameters, such as lag time and isotopic tracer steady state, may be determined and used as measurements of the protein's metabolism and physiology. Also, modeling may be performed on the data to fit multiple compartment models to estimate transfer between compartments. Of course, the type of mathematical modeling chosen will depend on the individual protein synthetic and clearance parameters (e.g., one-pool, multiple pools, steady state, non-steady-state, compartmental modeling, etc.).

The invention provides that the synthesis of protein is typically based upon the rate of increase of the labeled/unlabeled protein ratio over time (i.e., the slope, the exponential fit curve, or a compartmental model fit defines the rate of protein synthesis). For these calculations, a minimum of one sample is typically required (one could estimate the baseline label), two are preferred, and multiple samples are more preferred to calculate an accurate curve of the uptake of the label into the protein (i.e., the synthesis rate).

Conversely, after the administration of labeled amino acid is terminated, the rate of decrease of the ratio of labeled to unlabeled protein typically reflects the clearance rate of that protein. For these calculations, a minimum of one sample is typically required (one could estimate the baseline label), two are preferred, and multiple samples are more preferred to calculate an accurate curve of the decrease of the label from the protein over time (i.e., the clearance rate). The amount of labeled protein in a biological sample at a given time reflects the synthesis rate (i.e., production) or the clearance rate (i.e., removal or destruction) and is usually expressed as percent per hour or the mass/time (e.g., mg/hr) of the protein in the subject.

In an exemplary embodiment, as illustrated in the examples, the in vivo metabolism of amyloid-$\beta$ (A$\beta$) is measured by administering labeled leucine to a subject over 9 hours and collecting biological samples at regular intervals over 36 hours. The biological sample may be collected from blood plasma or CSF. The amount of labeled and unlabeled A$\beta$ in the biological samples is typically determined by immunopreciptitation followed by LC-ESI-tandem MS. From these measurements, the ratio of labeled to unlabeled A$\beta$ may be determined, and this ratio permits the determination of metabolism parameters, such as rate of synthesis and rate of clearance of A$\beta$.

II. Kits for Diagnosing or Monitoring the Progression or Treatment of Neurological and Neurodegenerative Diseases The current invention provides kits for diagnosing or monitoring the progression or treatment of a neurological or neurodegenerative disease by measuring the in vivo metabolism of a central nervous system-derived protein in a subject. Generally, a kit comprises a labeled amino acid, means for administering the labeled amino acid, means for collecting biological samples over time, and instructions for detecting and determining the ratio of labeled to unlabeled protein so that a metabolic index may be calculated. The metabolic index then may be compared to a metabolic index of a normal, healthy individual or compared to a metabolic index from the same subject generated at an earlier time. These comparisons may enable a practitioner to predict the advent of a neurological or neurodegenerative disease, diagnose the onset of a neurological or neurodegenerative disease, monitor the progression of a neurological or neurodegenerative disease, or verify the effectiveness of a treatment for a neurological or neurodegenerative disease. In a preferred embodiment, the kit comprises $^{13}C_6$-leucine or $^{13}C_6$-phenylalanine, the protein to be labeled is A$\beta$, and the disease to be assessed is AD.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

"Clearance rate" refers to the rate at which the biomolecule of interest is removed.

"Fractional clearance rate" or FCR is calculated as the natural log of the ratio of labeled biomolecule over a specified period of time.

"Fractional synthesis rate" or FSR is calculated as the slope of the increasing ratio of labeled biomolecule over a specified period of time divided by the predicted steady state value of the labeled precursor.

"Isotope" refers to all forms of a given element whose nuclei have the same atomic number but have different mass numbers because they contain different numbers of neutrons. By way of a non-limiting example, $^{12}C$ and $^{13}C$ are both stable isotopes of carbon.

"Lag time" generally refers to the delay of time from when the biomolecule is first labeled until the labeled biomolecule is detected.

"Metabolism" refers to any combination of the synthesis, transport, breakdown, modification, or clearance rate of a biomolecule.

"Metabolic index" refers to a measurement comprising the fractional synthesis rate (FSR) and the fractional clearance rate (FCR) of the biomolecule of interest. Comparison of metabolic indices from normal and diseased individuals may aid in the diagnosis or monitoring of neurological or neurodegenerative diseases.

"Neurally derived cells" includes all cells within the blood-brain-barrier including neurons, astrocytes, microglia, choroid plexus cells, ependymal cells, other glial cells, etc.

"Steady state" refers to a state during which there is insignificant change in the measured parameter over a specified period of time.

"Synthesis rate" refers to the rate at which the biomolecule of interest is synthesized.

In metabolic tracer studies, a "stable isotope" is a nonradioactive isotope that is less abundant than the most abundant naturally occurring isotope.

"Subject" as used herein means a living organism having a central nervous system. In particular, the subject is a mammal. Suitable subjects include research animals, companion animals, farm animals, and zoo animals. The preferred subject is a human.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Measurement of Amyloid-β Metabolism In Vitro

Rationale

Biochemical, genetic, and animal model evidence implicates Aβ (FIG. 1) as a pathogenic peptide in AD. In order to develop a method to measure Aβ in vivo labeling, an in vitro system was designed using four basic steps: 1) label Aβ in vitro in culture, 2) isolate Aβ from other labeled proteins, 3) specifically cleave Aβ into fragments that could be analyzed for the label, and 4) quantitate the labeled and unlabeled fragments.

Amyloid-β Immunoprecipitation and Cleavage

Figure 2:
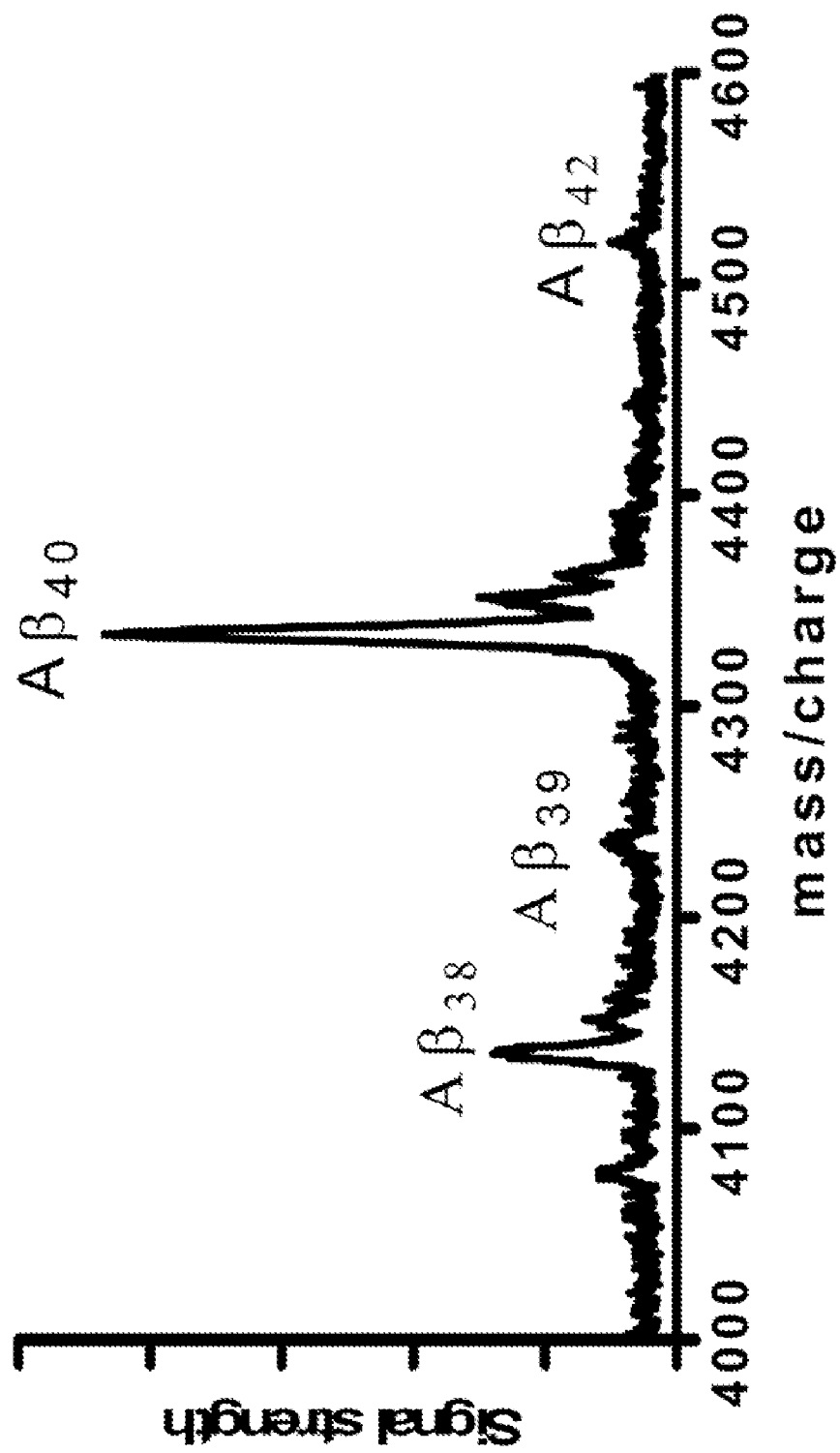
FIG. 2 depicts a mass spectrometer plot showing the separation of the amyloid-β peptides. Aβ peptides were immunoprecipitated from human CSF with the central domain anti-Aβ antibody, m266, and the eluted Aβ was subjected to mass spectrometry. Mass spectral peaks are labeled with their corresponding peptide variants; $A\beta_{38}$, $A\beta_{39}$, $A\beta_{40}$, and $A\beta_{42}$.

First, a method was developed for isolating and measuring unlabeled Aβ from biologic fluids. Aβ was immunoprecipitated from samples of CSF or cell culture media using a highly specific monoclonal antibody (m266), which recognizes the central domain (residues 13-28) of the molecules. Antibody beads were prepared by covalently binding m266 antibody to CNBr sepharose beads per the manufacturers protocol at a concentration of 10 mg/ml of m266 antibody. The antibody beads were stored at 4° C. in a slurry of 50% PBS and 0.02% azide. The immunoprecipitation mixture was 250 µl of 5×RIPA, 12.5 µl of 100× protease inhibitors, and 30 µl of antibody-bead slurry in an Eppendorf tube. To this, 1 ml of the biological sample was added and the tube was rotated overnight at 4° C. The beads were rinsed once with 1×RIPA and twice with 25 mM ammonium bicarbonate. They were aspirated dry after the final rinse and Aβ was eluted off the antibody-bead complex using 30 µl of pure formic acid. Aβ was directly characterized (molecular weight and amino acid sequence) using mass spectrometry. Results were similar to previously published findings (Wang et al. 1996, J. Biol. Chem. 271(50): 31894-31902), as shown in FIG. 2.

Amyloid-β may be cleaved into smaller fragments by enzymatic digestion using trypsin. Cleavage of Aβ by trypsin produces the $A\beta_{1-5}$, $A\beta_{6-16}$, $A\beta_{17-28}$, and $A\beta_{29-40/42}$ fragments, as depicted in FIG. 1.

Labeling of Amyloid-β

Second, a method was developed to label newly synthesized Aβ. $^{13}C_6$-leucine was used as a metabolic label because leucine equilibrates across the blood brain barrier quickly via active transport (Smith et al. 1987, J Neurochem 49(5): 1651-1658), is an essential amino acid, does not change the properties of Aβ, and is safe and nonradioactive. $^{13}C$ stable isotopes do not change the chemical or biologic properties of amino acids or proteins; only the mass weight is increased by one Dalton for each $^{13}C$ label. In fact, entire organisms have been grown on pure $^{13}C$ without any deleterious effect. The labeled leucine is incorporated into the amino acid sequence of Aβ at positions 17 and 34 (see FIG. 1).

The naturally occurring isotopes $^{13}C$ (1.1% of all carbon) and $^{15}N$ cause a natural distribution of mass of larger molecules, including proteins. Due to the size of Aβ and the presence of these naturally occurring isotopes, the peptide may be broken into smaller peptides for direct measurement of the label. Alternatively, separation may be made using whole undigested Aβ.

Liquid Chromatography/Mass Spectrometry

Figure 3A:
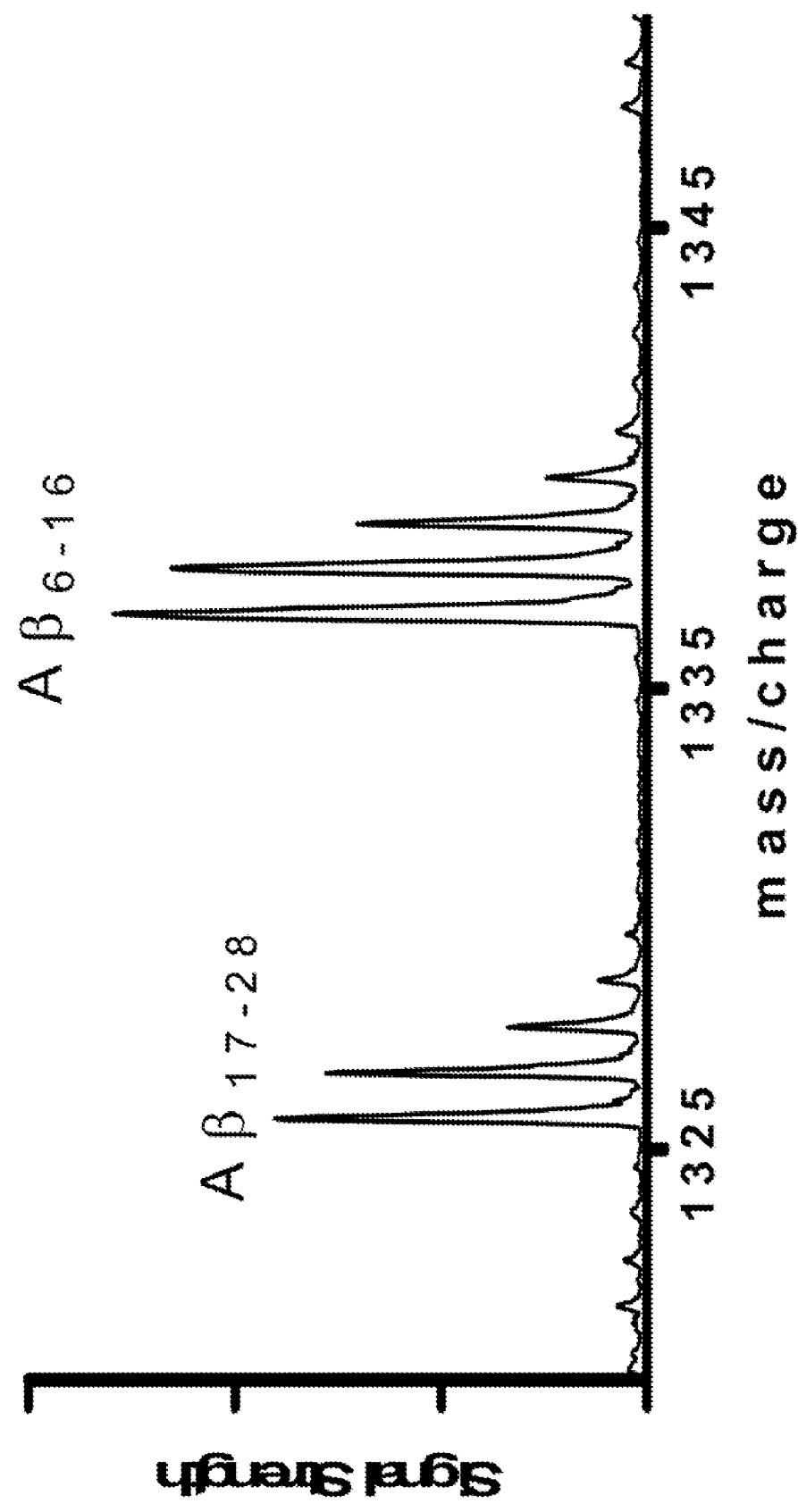
FIG. 3 presents mass spectrometer plots illustrating the shift in molecular weight of the $^{13}$C-labeled $A\beta_{17-28}$ fragment. In panel A, unlabeled media from a human neuroglioma cell line producing Aβ in vitro was collected and immunoprecipitated. Amyloid-beta peptides were then cleaved with trypsin at sites 5, 16, and 28 (see FIG. 1) producing the two fragment envelopes shown at masses 1325 and 1336. Note the two mass envelopes of Aβ fragments $A\beta_{17-28}$ (1325) and $A\beta_{6-16}$ (1336) showing the statistical distribution of natural isotopes in unlabeled Aβ. Also, note there is no signal at mass of 1331, where the labeled signal would be. In panel B, media from human neuroglioma cells cultured for 24 hours in the presence of $^{13}C_6$-leucine was collected and Aβ was immunoprecipitated and cleaved with trypsin to produce the fragment envelopes shown at masses 1325, 1331, and 1336. Note the shift of mass (arrow) of $A\beta_{17-28}$ from 1325 to 1331 that demonstrates the $^{13}C_6$-leucine labeled Aβ fragment ($A\beta^*_{17-28}$). $A\beta_{6-16}$ does not contain a leucine, and so is not labeled or mass shifted. A minor amount of $A\beta_{17-28}$ remains unlabeled.
Figure 3B:
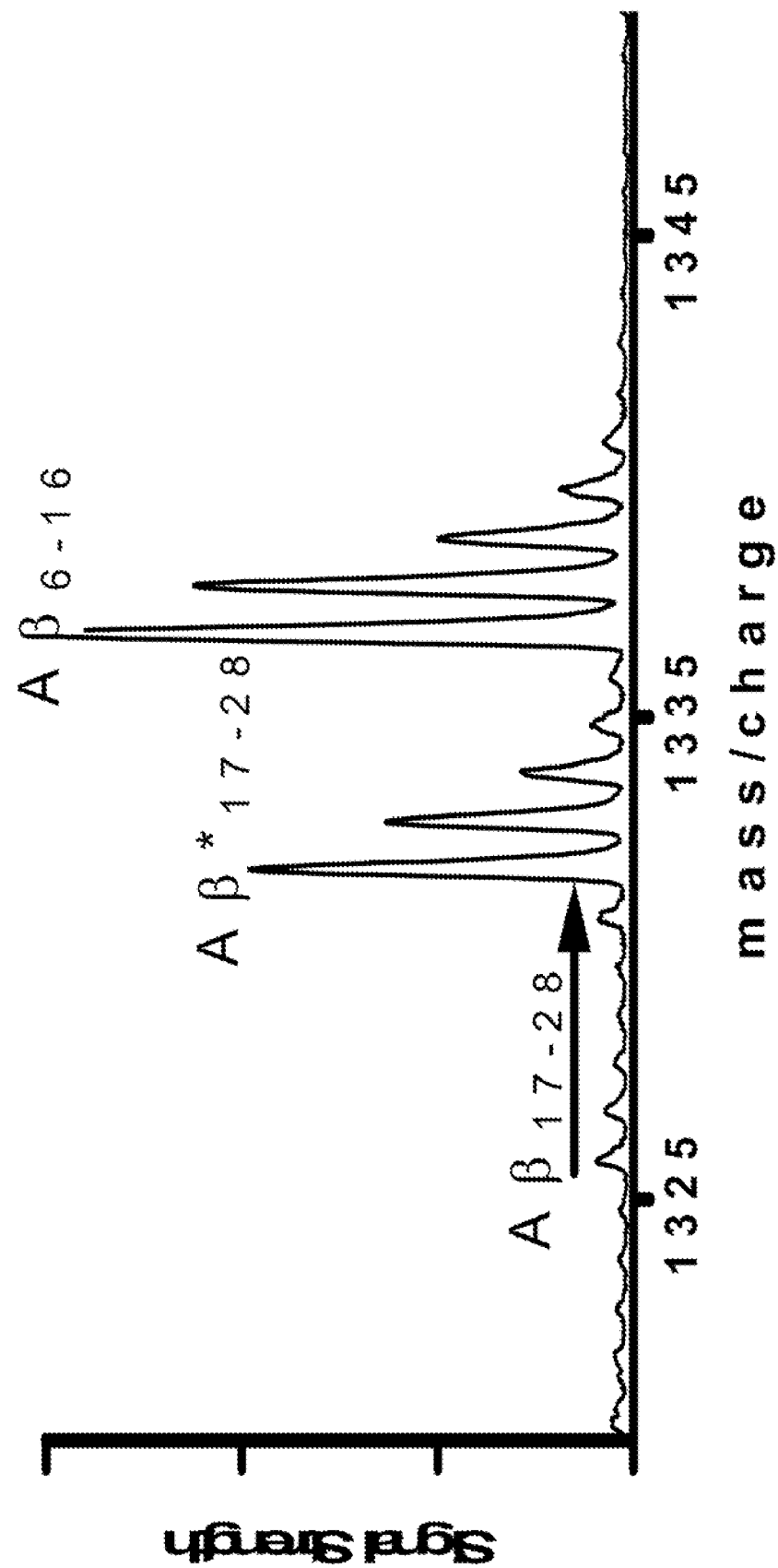

Third, a method to accurately quantitate labeled and unlabeled Aβ was developed. For this, a Waters (Milford, Mass.) capillary liquid chromatography system with auto injector was interfaced to a Thermo-Finnigan (San Jose, Calif.) LCQ-DECA equipped with an electrospray ionization source (LC-ESI-tandem MS). A 5 µl aliquot of each sample was injected onto a Vydac C-18 capillary column (0.3×150 mm MS 5 µm column). The Aβ$_{17-28}$ fragment contains one leucine residue and incorporation of $^{13}C_6$-leucine shifts the molecular weight of the fragment by 6 Daltons. In positive-ion scanning mode, LC-ESI-MS analysis of trypsin-digested synthetic and immunoprecipitated Aβ yielded the expected parent ions at masses 1325.2 for Aβ$_{17-28}$ and 1331.2 for $^{13}C_6$-leucine labeled Aβ$_{17-28}$ (FIGS. 3A and 3B). The percent of labeled Aβ (Aβ*) was calculated as the ratio of all labeled MS/MS ions from labeled Aβ$_{17-28}$ divided by all unlabeled MS/MS ions from unlabeled Aβ$_{17-28}$. A custom Microsoft Excel spreadsheet with macros was used to calculate the ratio as the tracer to tracee ratio (TTR) of Aβ$_{17-28}$ by the following formula:

$$TTR_{A\beta} = \frac{\sum MS/MS \text{ ions } A\beta^*_{17-28}}{\sum MS/MS \text{ ions } A\beta_{17-28}}$$

Figure 4:
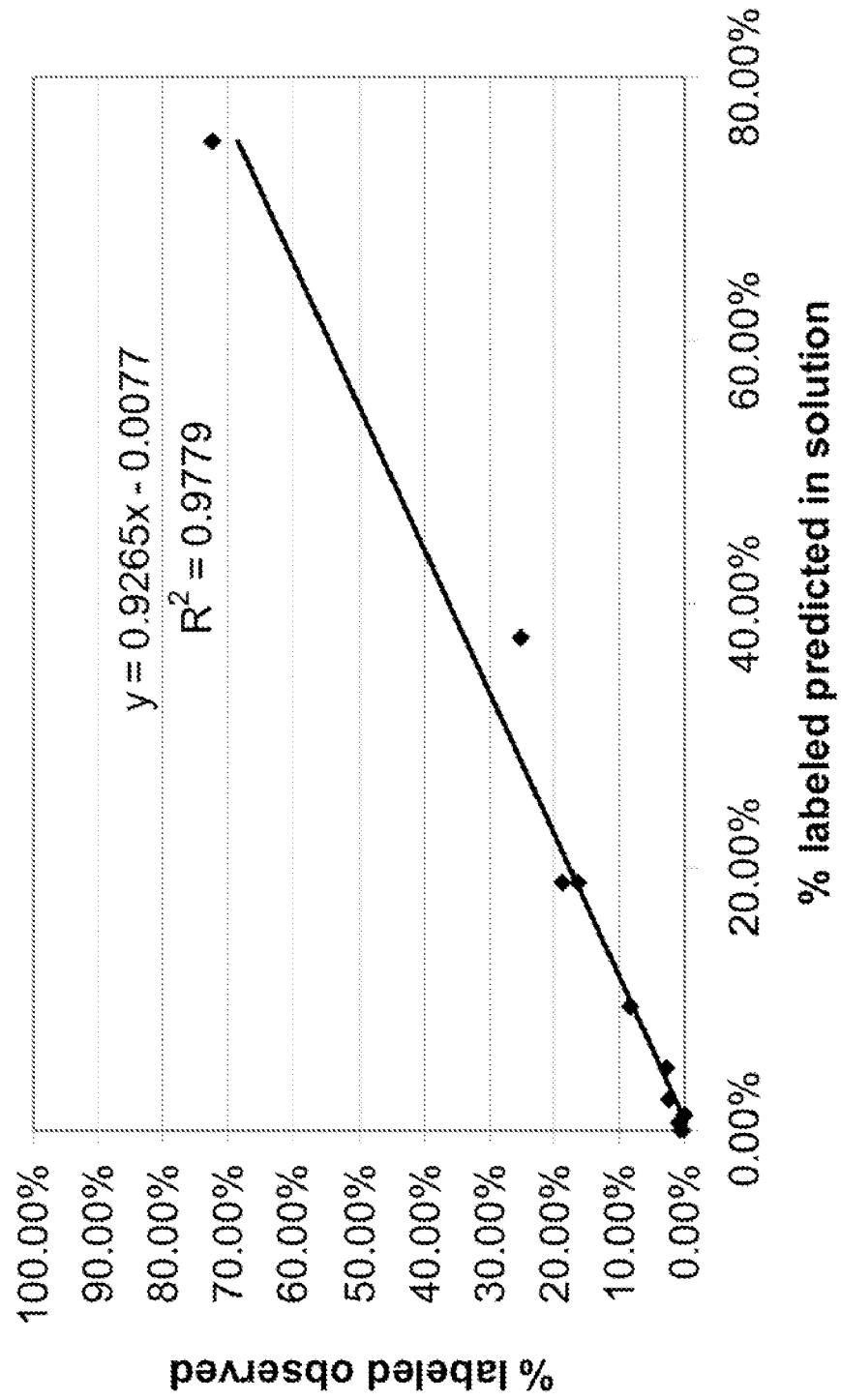
FIG. 4 depicts a graph showing a standard curve of the labeling of Aβ in vitro. A sample of labeled cultured media was serially diluted to generate a standard curve to test the linearity and variability of the measurement technique. The Aβ was precipitated from the media, trypsin digested, and the fragments were analyzed on a Liquid Chromatography Electro-Spray Injection (LC-ESI) mass spectrometer and the tandem mass spectra ions were quantitated using custom written software. The software summed both the labeled and the unlabeled tandem ions and calculated the ratio of labeled to total Aβ. The percent labeled Aβ versus the predicted value is shown with a linear regression line. Note the good linear fit, in addition to the low deviation.

It was concluded that this method provided a highly specific "fingerprint" of the Aβ in both labeled and unlabeled forms, as it quantitated the amounts of each form and determined the amino acid sequence at the same time. In this way, excellent separation and specificity of the labeled to unlabeled Aβ peptide was achieved. Accuracy and precision were tested by generating a standard curve from serial dilutions of labeled and unlabeled culture media (FIG. 4). The linear fit from a range of 0% to 80% labeled Aβ serial dilution standard curve gave an $R^2$ of 0.98 and slope of 0.92. Alternative measuring techniques that were evaluated included measuring parent ions directly in selective ion mode only and also using a MALDI-TOF mass spectrometer. However, these methods were unable to offer the sensitivity and specificity that was achieved by the LC-ESI using quantitative tandem mass spectrum analysis.

Amyloid-β In Vitro Labeling

Human neuroglioma cells that produce Aβ (Murphy et al. 2000, J. Biol. Chem. 275(34): 26277-26284) were grown in the presence of $^{13}C_6$-labeled leucine (Cambridge Isotope Laboratories, Cambridge, Mass.) or unlabeled leucine. Aβ was isolated from the media by immunoprecipitation with m266 antibody (see above). The eluted Aβ was digested with trypsin for 4 hours at 37° C., and the fragments were analyzed by LC-ESI MS. As expected, the Aβ$_{17-28}$ fragment of Aβ isolated from cells incubated in the presence of unlabeled leucine had a molecular weight of 1325.2 and the Aβ$_{17-28}$ fragment of Aβ isolated from $^{13}C_6$-labeled leucine incubated cells had a molecular weight of 1331.2 (FIG. 3B). These findings indicate that the cells incorporated $^{13}C_6$-leucine into Aβ, confirming that Aβ synthesized in the presence of $^{13}C_6$-leucine incorporates the labeled amino acid and that the shift of 6 Daltons in the molecular weight of the leucine-containing peptide can be distinguished using mass spectrometry.

Cell culture media at 4 hours and 24 hours of $^{13}C_6$-leucine labeling were analyzed to determine the relative amount of labeling that occurs as a function of time. The 4-hour labeling experiment revealed approximately 70% labeling, while the 24-hour labeling experiment revealed more than 95% labeling. These findings indicate that within hours after exposure to the label, amyloid precursor protein (APP) incorporated the labeled amino acid, and the labeled Aβ was cleaved from labeled APP and released into the extracellular space.

Example 2

Measurement of Amyloid-β Metabolism In Vivo

Rationale

Protein production and clearance are important parameters that are tightly regulated and reflect normal physiology as well as disease states. Previous studies of protein metabolism in humans have focused on whole body or peripheral body proteins, but not on proteins produced in the central nervous system (CNS). No methods were previously available to quantify protein synthesis or clearance rates in the CNS of humans. Such a method would be valuable to assess not only Aβ synthesis or clearance rates in humans but also the metabolism of a variety other proteins relevant to diseases of the CNS. In order to address critical questions about underlying AD pathogenesis and Aβ metabolism, a method for quantifying Aβ fractional synthesis rate (FSR) and fractional clearance rate (FCR) in vivo in the CNS of humans was developed.

Participants and Sampling

Figure 5:
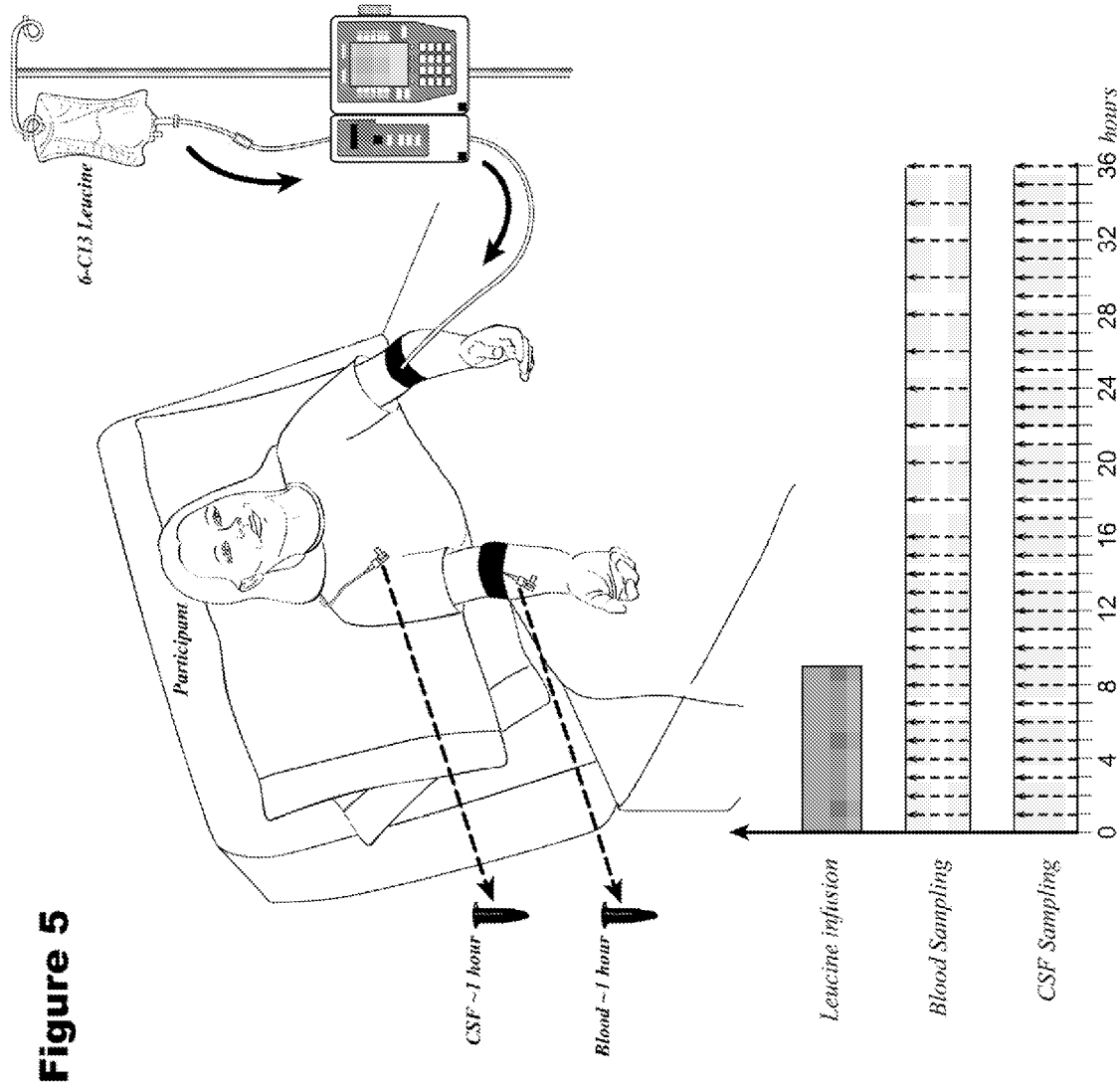
FIG. 5 depicts a schematic illustrating the in vivo labeling protocol. Shown is a diagram of participant with an intravenous catheter in either antecubital vein and a lumbar catheter in the L3-4 intrathecal space. In one IV, $^{13}C_6$-labeled leucine was infused at a rate of 1.8 to 2.5 mg/kg/hr for 9 or 12 hours, after an initial bolus of 2 mg/kg. Twelve ml of plasma was obtained through the other IV every hour for the first 16 hours and every other hour thereafter as depicted. Six ml of CSF was obtained through the lumbar catheter every hour. Each sample was then processed by immunoprecipitation of Aβ, trypsin digestion, and LC-ESI-MS analysis to determine the percent of labeled Aβ at each time point.

All human studies were approved by the Washington University Human Studies Committee and the General Clinical Research Center (GCRC) Advisory Committee. Informed consent was obtained from all participants. All participants were screened to be in good general health and without neurologic disease. Seven men and three women (23-45 yrs old) participated. Each research participant was admitted to the GCRC at 7:00 AM after an overnight fast from 8 PM the preceding evening. The GCRC Research Kitchen provided meals (60% carbohydrate, 20% fat, 20% protein, low leucine diet during labeled leucine infusion) at 9 AM, 1 PM, and 6 PM and the participant had free access to water. All food and water consumption was recorded during the admission by nursing staff and the GCRC kitchen. One intravenous catheter was placed in an antecubital vein and used to administer the stable isotope labeled leucine solution. A second intravenous catheter was placed in the contra-lateral antecubital vein to obtain blood samples. A subarachnoid catheter was inserted at the L3-L4 interspace via a Touhy needle, so that CSF could be sampled without performing multiple lumbar punctures (Williams, 2002, Neurology 58: 1859-1860). The intravenous catheters were placed by trained registered nurses and the lumbar catheter was placed by trained physicians with extensive experience in inserting catheters into the lumbar subarachnoid space. Blood samples were obtained hourly, unless the study was 36 hours, in which case, blood was obtained hourly for the first 16 hours and every other hour thereafter. CSF samples were obtained hourly throughout the study. See the schematic of the in vivo experimental protocol presented in FIG. 5. The participants were encouraged to stay in bed except to use the restroom.

$^{13}C_6$-leucine (Cambridge Isotope Laboratories) was dissolved in medical grade normal saline and then filtered through a 0.22 micron filter the day before each study. The labeled leucine was infused intravenously using a medical IV pump at a rate of 1.8 to 2.5 mg/kg/hr.

In Vivo Labeling and Quantitation of Aβ in One Participant

Figure 6A:
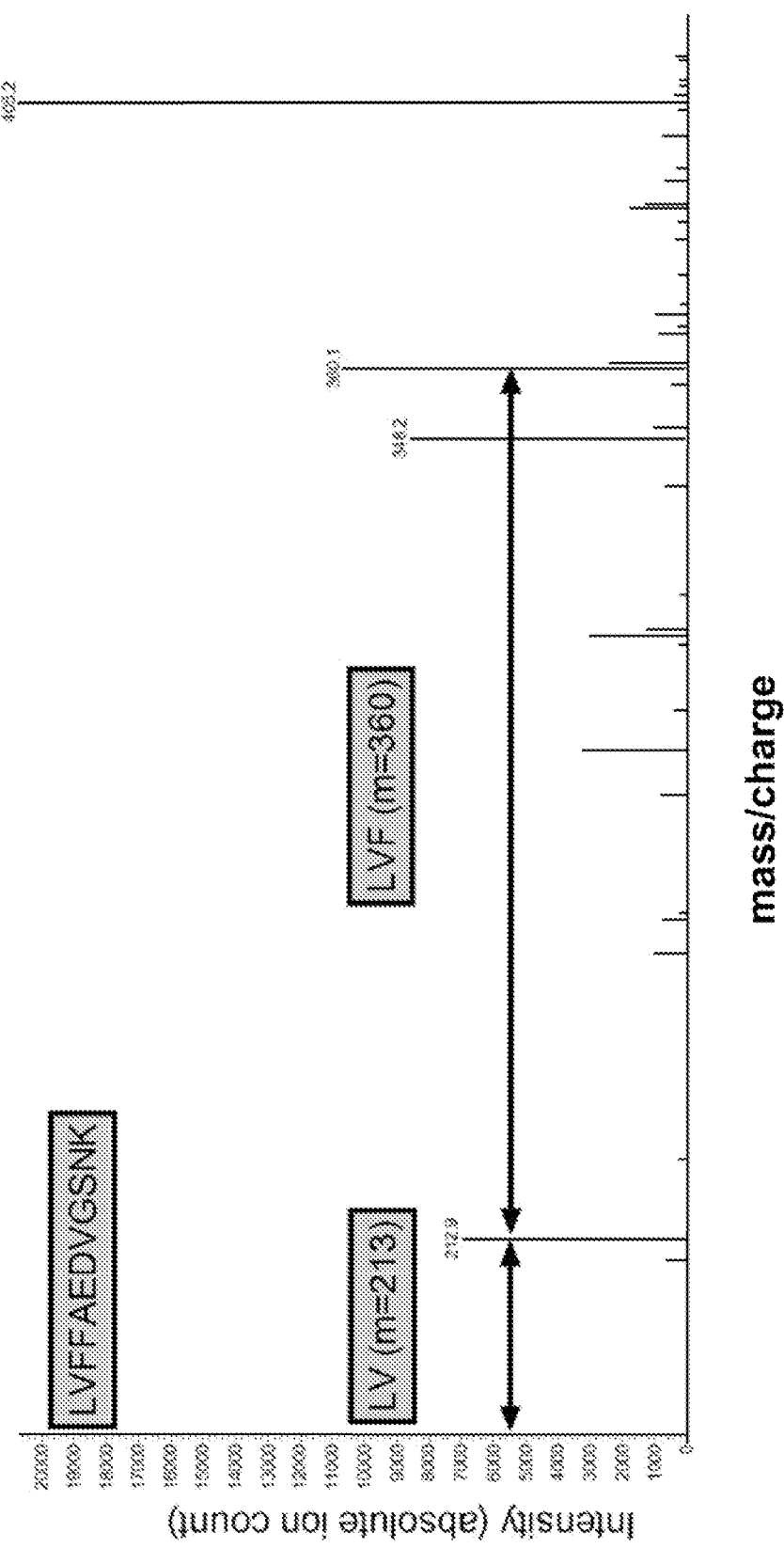
FIG. 6 depicts mass spectrometer plots demonstrating the MS/MS ions of labeled and unlabeled amyloid-β. Human CSF was collected after intravenous infusion of $^{13}C_6$-leucine. Representative spectra of unlabeled (a) and labeled (b) $Aβ_{17-28}$ (LVFFAEDVGSNK (SEQ ID NO:2)) are shown. The spectra were obtained using MS/MS analysis of unlabeled parent ion $Aβ_{17-28}$ at m/z 663.3 or labeled parent ion $Aβ_{17-28}$ at m/z 666.3. Note the MS/MS ions containing $^{13}C$-leucine ($Aβ_{17}$) are mass shifted by 6 Daltons demonstrating the labeled leucine. The Aβ ions without leucine at position 17 are not labeled and are not mass shifted by 6 Daltons.
Figure 6B:
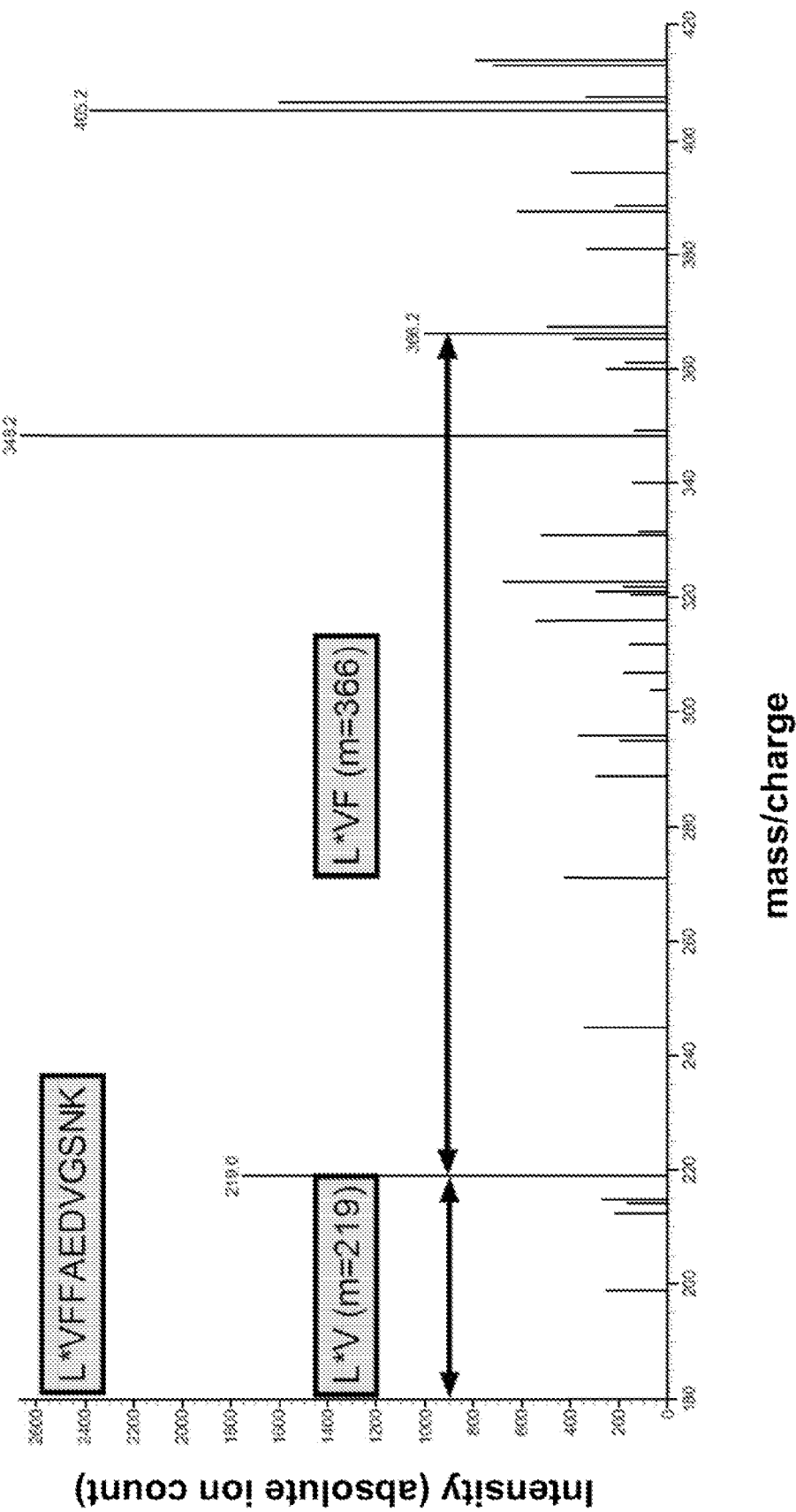

To determine if labeled Aβ could be produced and detected in vivo in a human, a single participant underwent a 24-hour infusion of labeled leucine followed by a lumbar puncture to obtain CSF. $^{13}C_6$-labeled leucine was infused at a rate of 1.8 mg/kg/hr in one IV. Every hour, 10 ml of plasma was obtained through the other IV. After 24 hours of continuous infusion, a single lumbar puncture was performed and 30 ml of CSF was obtained. Aβ was immunoprecipitated from the CSF sample, digested with trypsin, and a 5 μl aliquot of each sample was injected into a Vydac C-18 capillary column (0.3×150 mm MS 5 μm). In positive-ion scanning mode, LC-ESI-MS analysis of trypsin-digested synthetic and immunoprecipitated Aβ yielded the expected parent ions at masses 1325.2 for Aβ$_{17-28}$ and 1331.2 for $^{13}$C$_6$-leucine labeled Aβ$_{17-28}$. To obtain amino acid sequence and abundance data, these parent ions were subjected to collision induced dissociation (CID 28%), and tandem MS analysis of their doubly-charged species ([M+2H]$^{+2}$; m/z 663.6 and 666.6) were scanned in selected reaction monitoring mode (SRM), so that the y- and b-series ions generated were used for isotope ratio quantitation (FIG. 6). In addition, plasma and CSF $^{13}$C$_6$-leucine were measured to determine the maximum amount of $^{13}$C$_6$-leucine Aβ to be expected. The results demonstrated that unlabeled Aβ$_{17-28}$ and $^{13}$C-labeled Aβ$_{17-28}$ could be detected and measured in human CSF.

The results of the first human participant demonstrated three significant findings: 1) plasma $^{13}$C$_6$-leucine averaged 12% of total plasma leucine at an IV infusion rate of 1.8 mg/kg/hour; 2) CSF $^{13}$C$_6$-leucine was measured in CSF demonstrating a similar level (11.9%) as plasma at 24 hours; and 3) Aβ was labeled with $^{13}$C$_6$-leucine in human CSF at approximately 8% of total Aβ levels at 24 hours.

Figure 7:
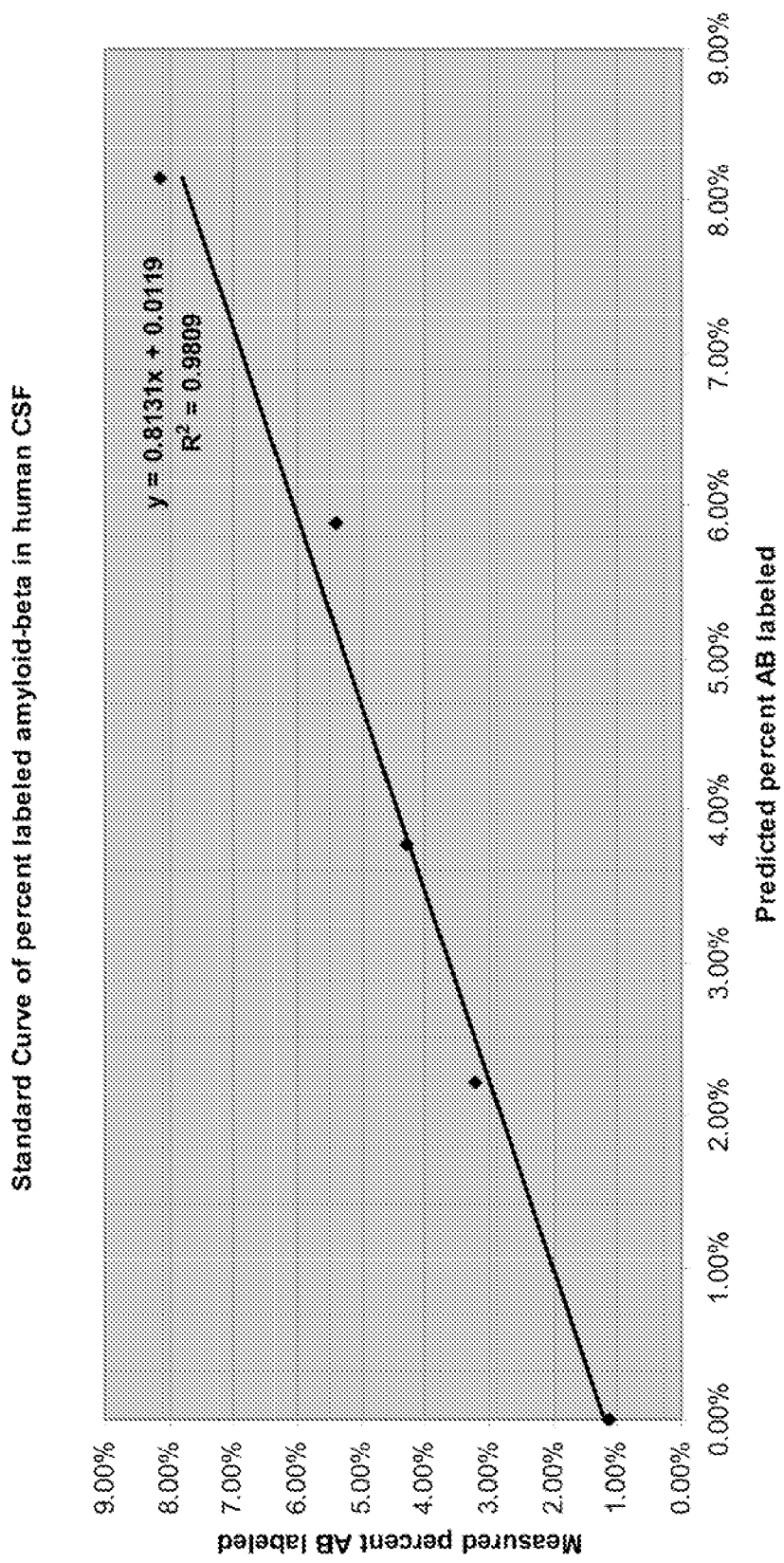
FIG. 7 depicts a graph showing a standard curve of the labeling of Aβ in vivo. A sample of labeled human CSF was serially diluted with unlabeled human CSF to generate a standard curve to quantify the accuracy and precision of the measurement technique for in vivo labeled Aβ in human CSF. The Aβ was precipitated from the CSF, trypsin digested, and the Aβ fragments were analyzed on a LC-ESI mass spectrometer and the tandem mass spectra ions were quantitated using custom written software. The software summed both the labeled and the unlabeled tandem ions and calculated the ratio of labeled to total Aβ. The predicted percent labeled Aβ versus the measured value is shown with a linear regression line. Note the good linear fit.

In order to quantify the accuracy and precision of the measurement technique of in vivo labeled Aβ in human CSF, a standard curve was generated from serial dilutions of labeled and unlabeled human CSF (FIG. 7). The measurement technique was the same as for the in vitro standard curve (FIG. 4). LC-ESI MS was used to quantitate the amounts of labeled and unlabeled Aβ$_{17-28}$ in selective ion monitoring mode with tandem mass spectrometer recording MS-2 ions. The linear fit from a range of 0% to 8% labeled Aβ serial dilution standard curve gave an R$^2$ of 0.98 and slope of 0.81. From these data, it was predicted that in vivo samples from human participants will likely range from 1 to 10% labeling. Note, the 1% measurement in unlabeled CSF at the Y-axis, whereas 0% was predicted. Due to the baseline noise of the detection system, it was not possible to measure less than 1% labeling with this system. It was concluded that Aβ can be labeled in vivo in humans and measured with good accuracy and precision using LC-ESI mass spectrometry.

Pharmacokinetics of In Vivo Labeling

To ensure that detectable $^{13}$C$_6$-leucine labeling of Aβ was achieved and maintained for an adequate period of time so that steady-state equations could be used to calculate Aβ synthesis and clearance rates, the optimal labeling and sampling times were determined. A range of $^{13}$C$_6$-leucine intravenous infusion dosages (1.8 to 2.5 mg/kg/hr), durations (6, 9, or 12 hours) and CSF/blood sampling times (from 12 to 36 hours duration) were tested (see Table 1).

TABLE 1

Participant Labeling and Sampling Parameters

| Participant Number | Infusion Dosage (mg/kg/hr) | Infusion Duration, hours | CSF/blood sampling, hours |
| --- | --- | --- | --- |
| 1 | 1.8 | 24 hours | 1 time at 24 hours |
| 2 | 1.9 | 12 hours | 24 hours |
| 3 | 2.5 | 12 hours | 13 hours |
| 4 | 2.5 | 9 hours | 24 hours |
| 5 | 2.4 | 6 hours | 6 hours |
| 6 | 2 | 6 hours | 36 hours |
| 7 | 2 | 6 hours | 36 hours |
| 8 | 2 | 9 hours | 36 hours |
| 9 | 2 | 9 hours | 36 hours |
| 10 | 2 | 9 hours | 36 hours |

Figure 8:
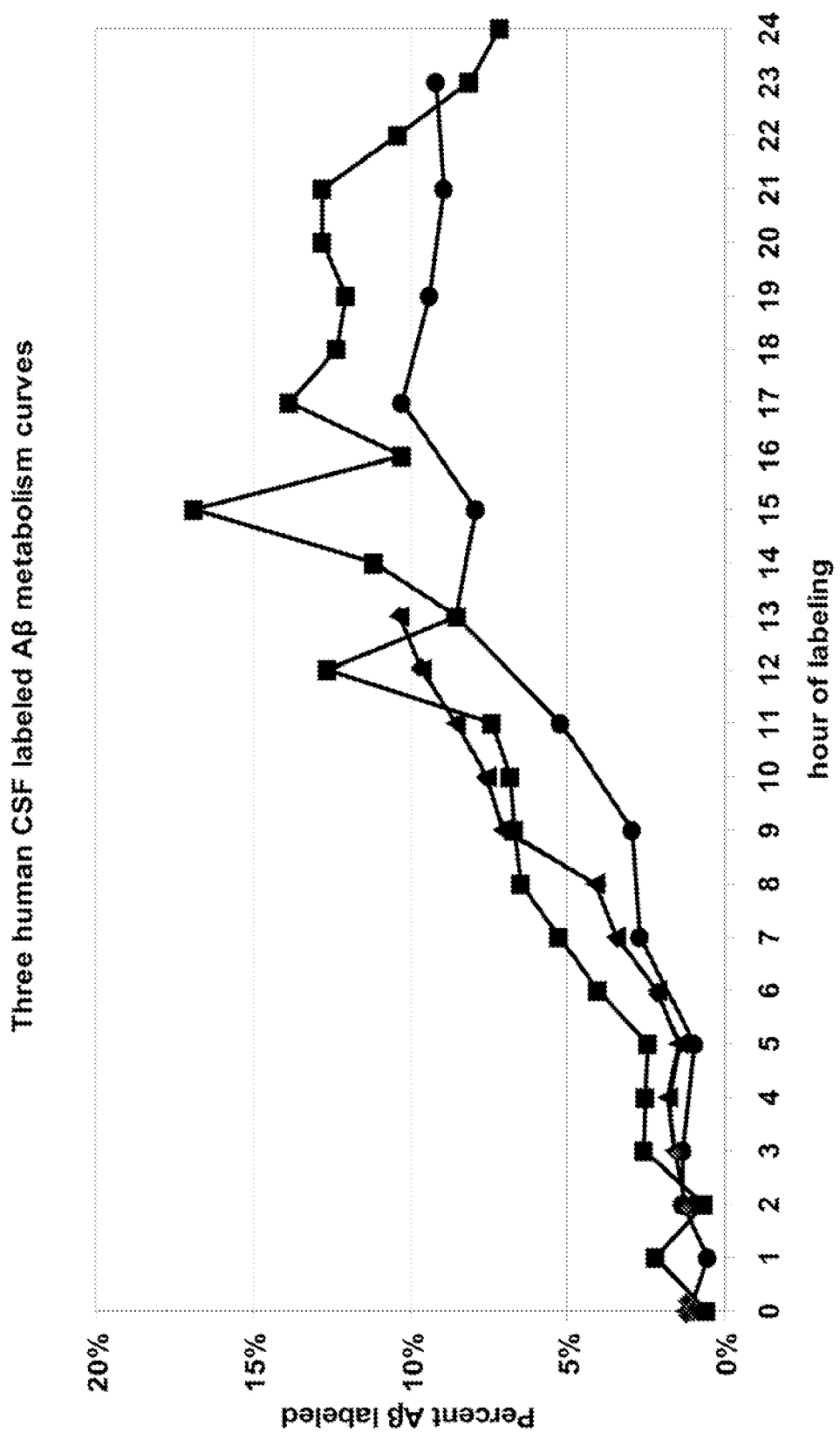
FIG. 8 depicts a graph illustrating the Aβ metabolism curves of three participants. Each participant started the labeled leucine infusion at time zero and continued for 9 (squares) or 12 hours (triangles and circles). Hourly samples of CSF were obtained through a lumbar catheter. Aβ was immunoprecipitated and trypsin digested. The percent of labeled Aβ was determined by measuring labeled and unlabeled tandem mass spectra ions on a LC-ESI mass spectrometer as described above.

Aβ metabolic labeling curves of three participants are presented in FIG. 8. $^{13}$C$_6$-labeled leucine was infused through one IV at a rate of 1.9 (circles), 2.5 (triangles), or 2.5 (squares) mg/kg/hr for 12 (circles, triangles) or 9 (squares) hours. Each hour, 10 ml of plasma and 6 ml of CSF were obtained through the other IV and the lumbar catheter, respectively. There was a 5-hour lag time before significant rises in labeled Aβ was detected. This was followed by a 9 (squares) or 12 (triangles or circles) hour increase in labeled Aβ until it plateaued for another 5 hours. The 9 hours of labeling (squares) had decreasing levels of labeled Aβ for the last 3 hours, while 12 hours of labeling (triangles or circles) did not show a decrease in labeled Aβ.

Additional studies revealed that labeled Aβ could be reliably quantified after 9 or 12 hours of label infusion, but not after 6 hours of label infusion. The synthesis portion of a labeling curve could be determined in the first 12 hours of sampling; however, the clearance portion of the labeling curve could only be determined with 36 hours of sampling. Based on these results, optimal labeling parameters for Aβ were defined to be 9 hours of IV infusion of the label and 36 hours of sample collection. These parameters allowed for assessment of both the fractional synthesis rate (FSR) and fractional clearance rate (FCR) portions of a labeling curve.

In Vivo Labeling Protocol

In the last three participants, $^{13}$C$_6$-labeled leucine was administered with an initial bolus of 2 mg/kg over 10 minutes to reach a steady state of labeled leucine, followed by 9 hours of continuous intravenous infusion at a rate of 2 mg/kg/hr. Blood and CSF were sampled for 36 hours in the last 3 participants. Serial samples of 12 ml blood and 6 ml CSF were taken at one or two hour time intervals. CSF has a production rate of ~20 ml per hour (Fishman R A, 1992, Cerebrospinal fluid in diseases of the nervous system, Saunders, Philadelphia) in a normal sized adult and replenishes itself throughout the procedure. Over a 36-hour study, the total amount of blood collected was 312 ml and the total amount of CSF collected was 216 ml.

There were a total of 10 participants enrolled in the study, with 8 completing the predefined protocols and 2 studies stopped before completion due to post-lumbar puncture headache associated with the study (see Table 1). Two of the 8 completed studies had a 6 hour labeled leucine infusion, and labeled Aβ levels in these 2 participants were too low to accurately measure and were not used for analysis. Thus, the findings from the remaining 6 studies are reported below.

Labeled Leucine Quantitation

Figure 9:
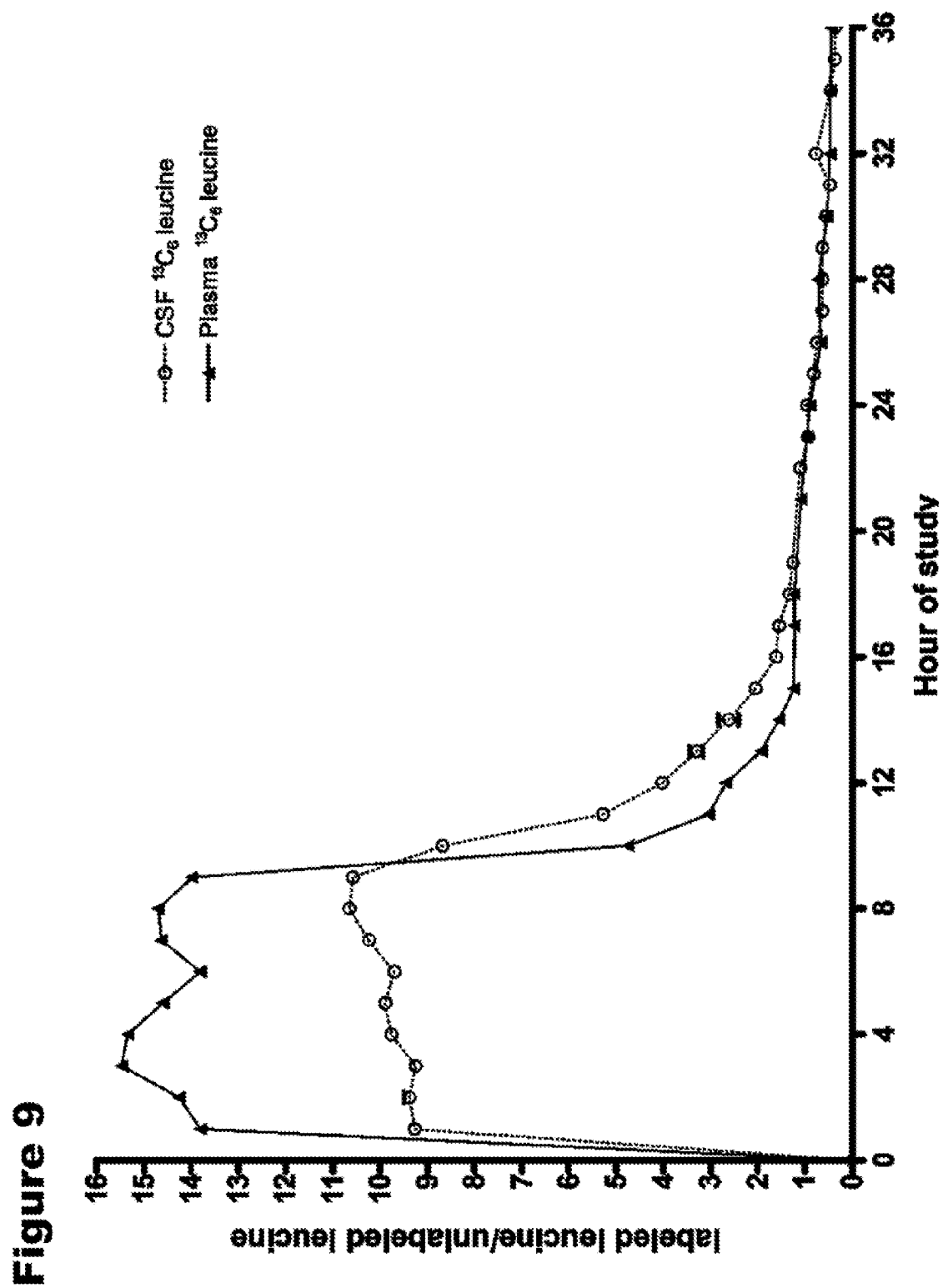
FIG. 9 depicts a graph illustrating the ratio of labeled leucine in the CSF and blood from a participant during a 36-hour study. The CSF and plasma labeled leucine levels reached near steady state within an hour of the initial bolus of 2 mg/kg. After the infusion of labeled leucine into the bloodstream was stopped at 9 hours, there was an exponential decay in labeled leucine levels. The plasma level of labeled leucine was about 4% higher than the CSF labeled leucine levels during the infusion period.

Plasma and CSF samples were analyzed to determine the amount of labeled leucine present in each fluid (FIG. 9). The labeled to unlabeled leucine ratios for plasma and CSF $^{13}$C$_6$-leucine were quantified using capillary gas chromatography-mass spectrometry (GC-MS) (Yarasheski et al. 2005, Am J. Physiol. Endocrinol. Metab. 288: E278-284; Yarasheski et al. 1998 Am J. Physiol. 275: E577-583), which is more appropriate than LC-ESI-MS for low mass amino acid analysis. The $^{13}$C$_6$-leucine reached steady state levels of 14% and 10% in both plasma and CSF, respectively, within an hour. This confirmed that leucine was rapidly transported across the blood-brain-barrier via known neutral amino acid transporter systems (Smith et al. 1987 J. Neurochem. 49(5): 1651-1658).

Labeled Aβ Dynamics

Figure 10:
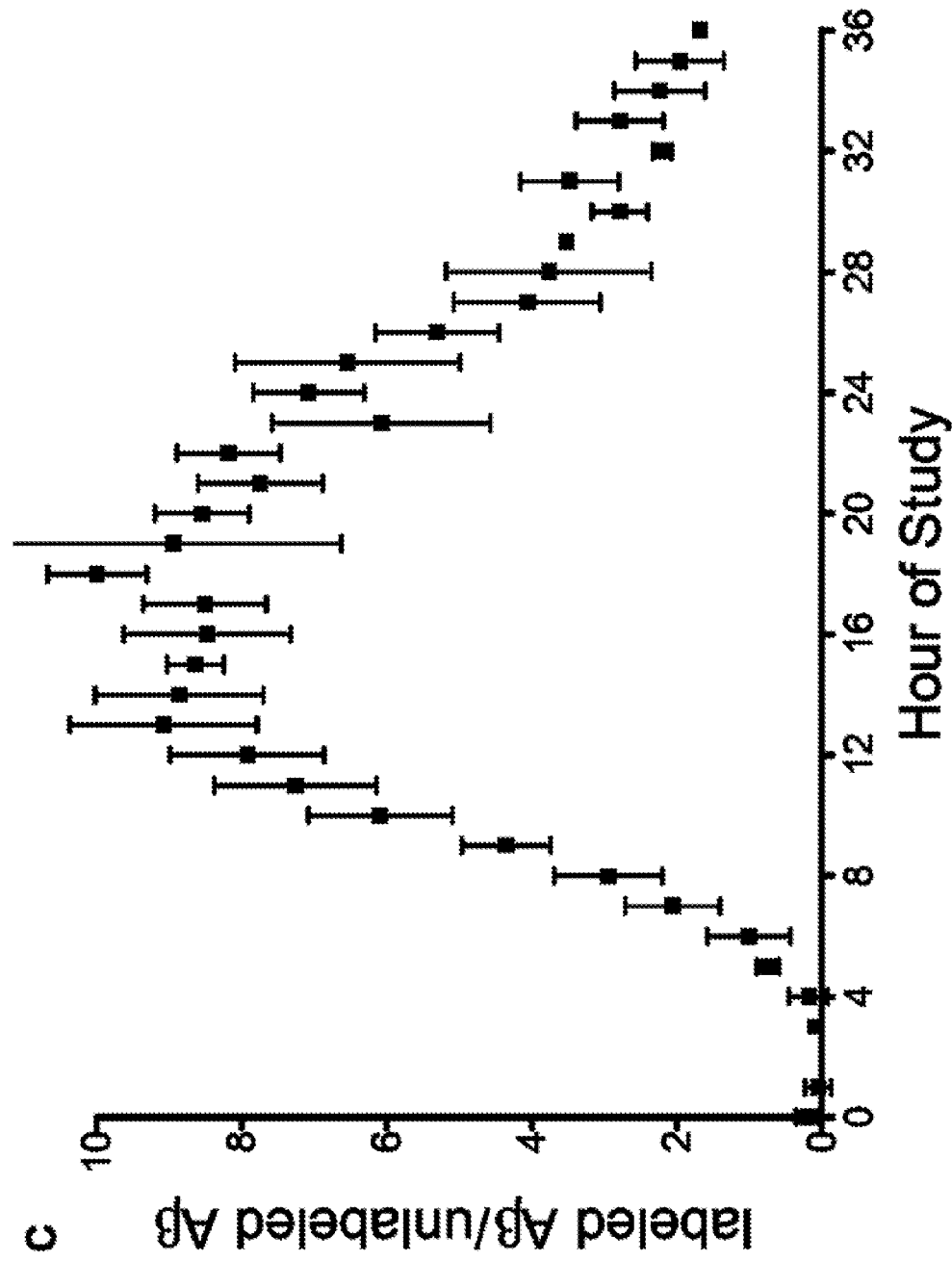
FIG. 10 depicts a graph illustrating the mean ratio of labeled to unlabeled Aβ in CSF from 6 participants over 36 hours. The labeled to unlabeled Aβ metabolism curves were averaged and the mean for each time point is shown +/−SEM. Each participant was labeled for 9 or 12 hours, while sampling occurred hourly from 0 to 12, 24, or 36 hours. There was no detectable incorporation of label during the first 4 hours, followed by an increase in percent labeled Aβ that plateaued to near steady state labeled leucine levels (~10%) before decreasing over the last 12 hours of the study.

For each hourly sample of CSF collected, the ratio of labeled to unlabeled Aβ was determined by immunoprecipitation-MS/MS, as described above. The MS/MS ions from $^{13}$C$_6$-labeled Aβ$_{17-28}$ were divided by the MS/MS ions from unlabeled Aβ$_{17-28}$ to produce a ratio of labeled Aβ to unlabeled Aβ (see TTR formula, above). The mean labeled Aβ ratio and standard error (n=6) of each time point are shown in FIG. 10. There was no measurable labeled Aβ for the first 4 hours, followed by an increase from 5 to 13 hours. There was no significant change from 13 to 24 hours. The labeled Aβ decreased from 24 to 36 hours.

Figure 11A:
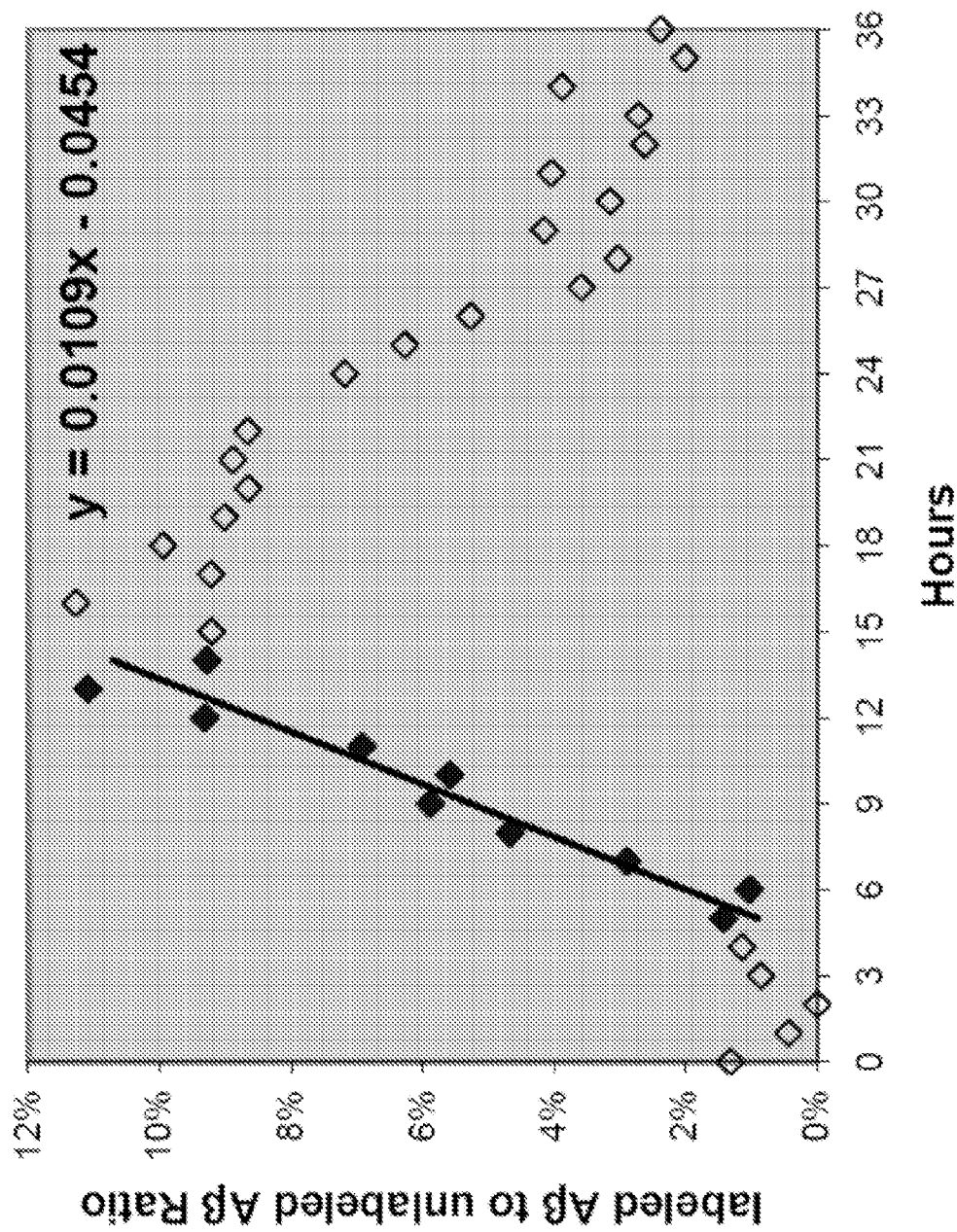
FIG. 11 depicts graphs showing the Aβ metabolism curves from 3 participants with 9-hour label infusion and 36 hour sampling. Panels A-C depict calculation of the fractional synthesis rate (FSR), which was calculated by the slope of increasing labeled Aβ divided by the predicted steady state value. The predicted steady state value was estimated as the average CSF labeled leucine measured during labeling. The slope was defined to start after the 4 hours lag time when there was no increase in labeled Aβ and ending 9 hours later (solid diamonds). Panels D-F show the calculation of the fractional clearance rate (FCR), which was calculated by the slope of the natural logarithm of percent labeled Aβ from hours 24 to 36 (solid diamonds).
Figure 11B:
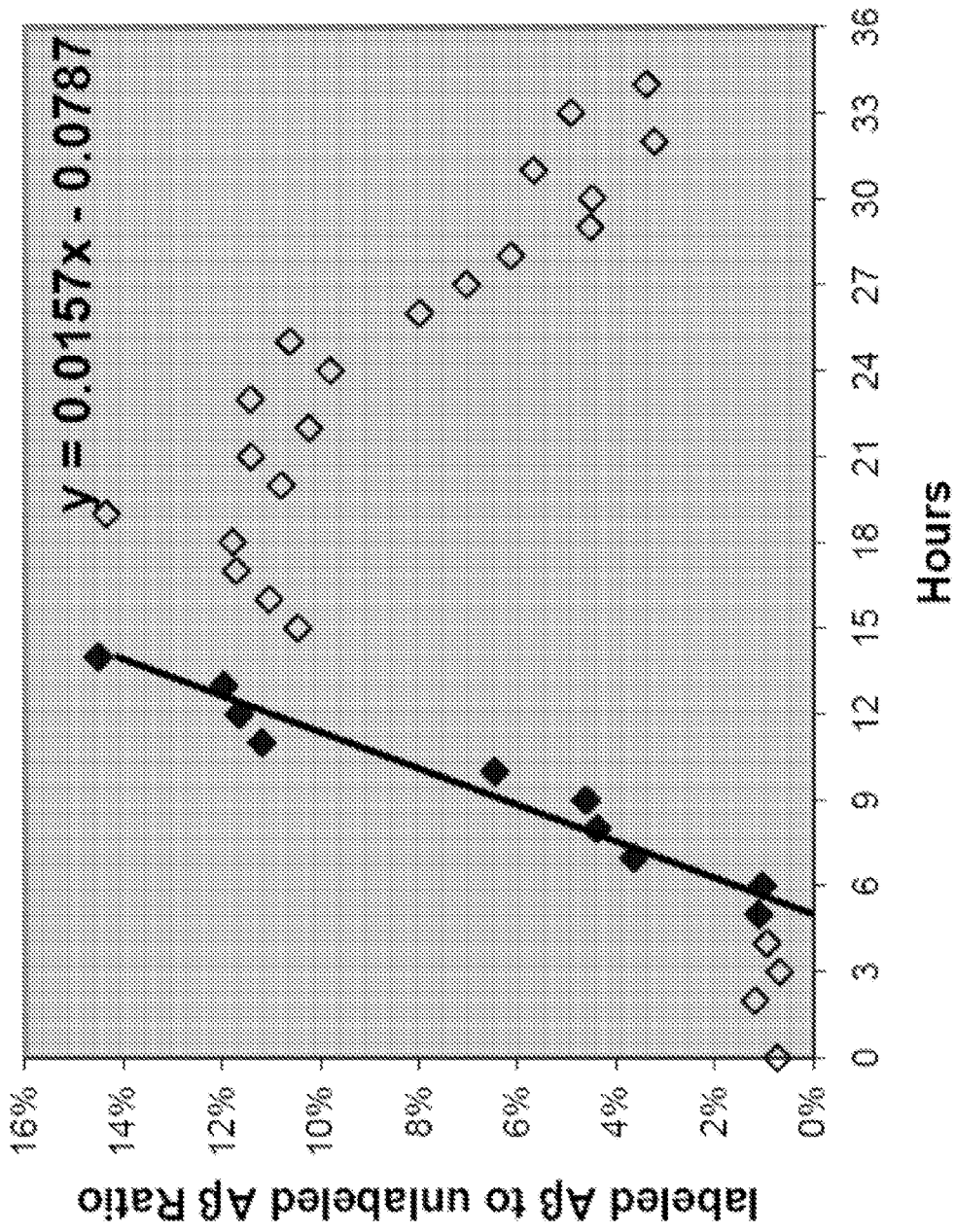
Figure 11C:
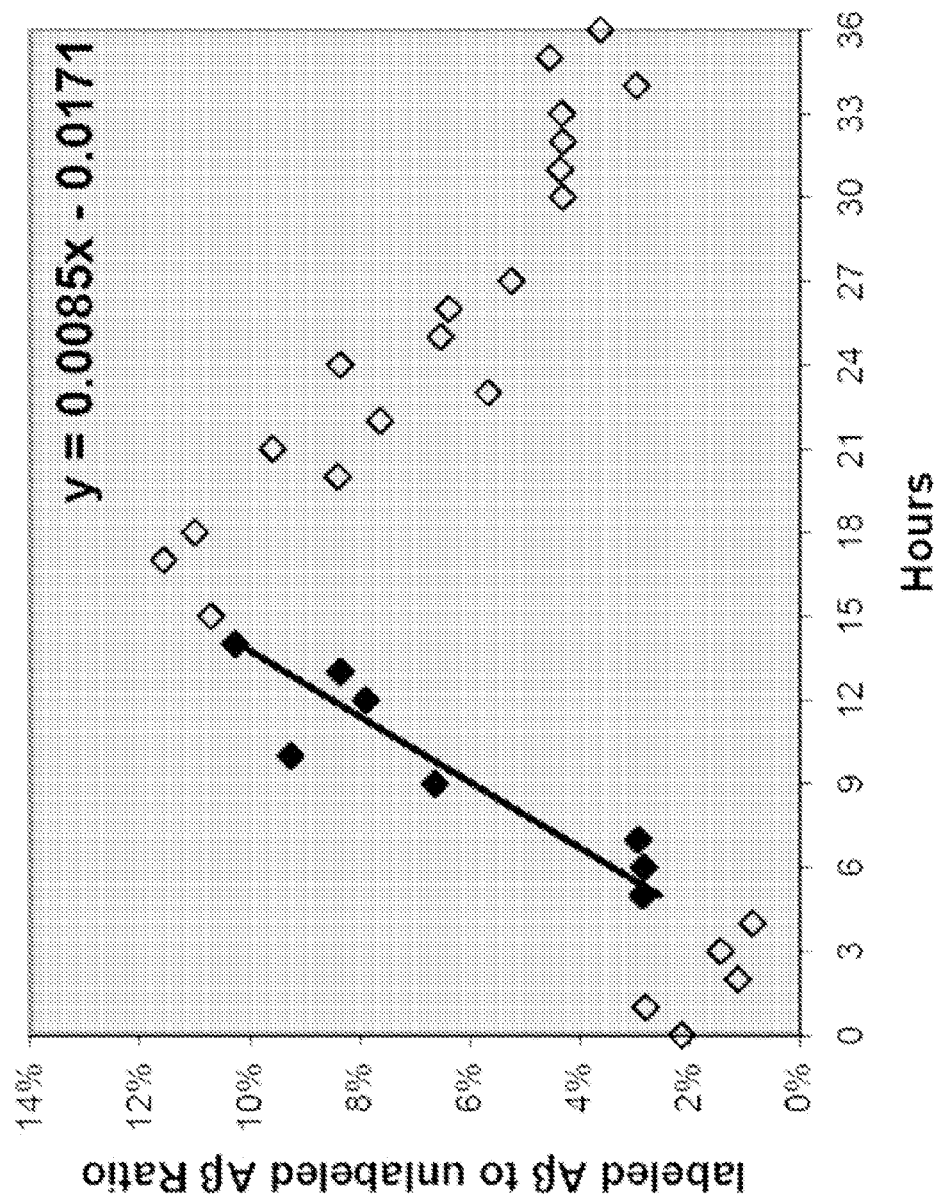

Calculation of FSR and FCR:

The fractional synthesis rate (FSR) was calculated using the standard formula, presented below:

$$FSR = \frac{(E_{t2} - E_{t1})_{A\beta}}{(t_2 - t_1)} \div \text{Precursor } E$$

Where $(E_{t2}-E_{t1})_{A\beta}/(t_2-t_1)$ is defined as the slope of labeled Aβ during labeling and the Precursor E is the ratio of labeled leucine. FSR, in percent per hour, was operationally defined as the slope of the linear regression from 6 to 15 hours divided by the average of CSF $^{13}C_6$-labeled leucine level during infusion (see FIG. 11A-C). For example, a FSR of 7.6% per hour means that 7.6% of total Aβ was produced each hour.

The fractional clearance rate (FCR) was calculated by fitting the slope of the natural logarithm of the clearance portion of the labeled Aβ curve, according to the following formula:

$$FCR = \ln\left(\frac{\Delta TTR_{A\beta}}{\Delta \text{time(hours)}_{24-36}}\right)$$

Figure 11D:
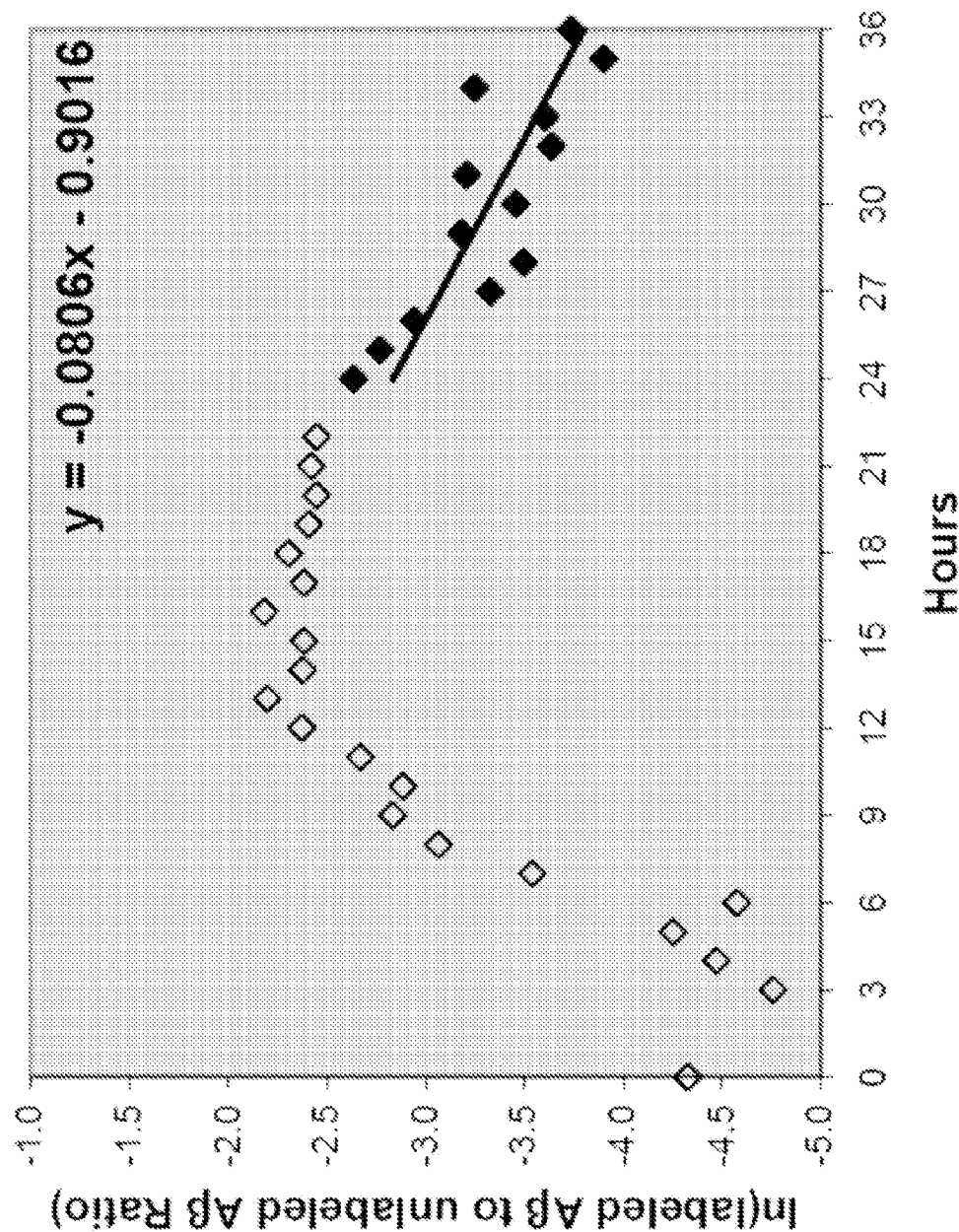
Figure 11E:
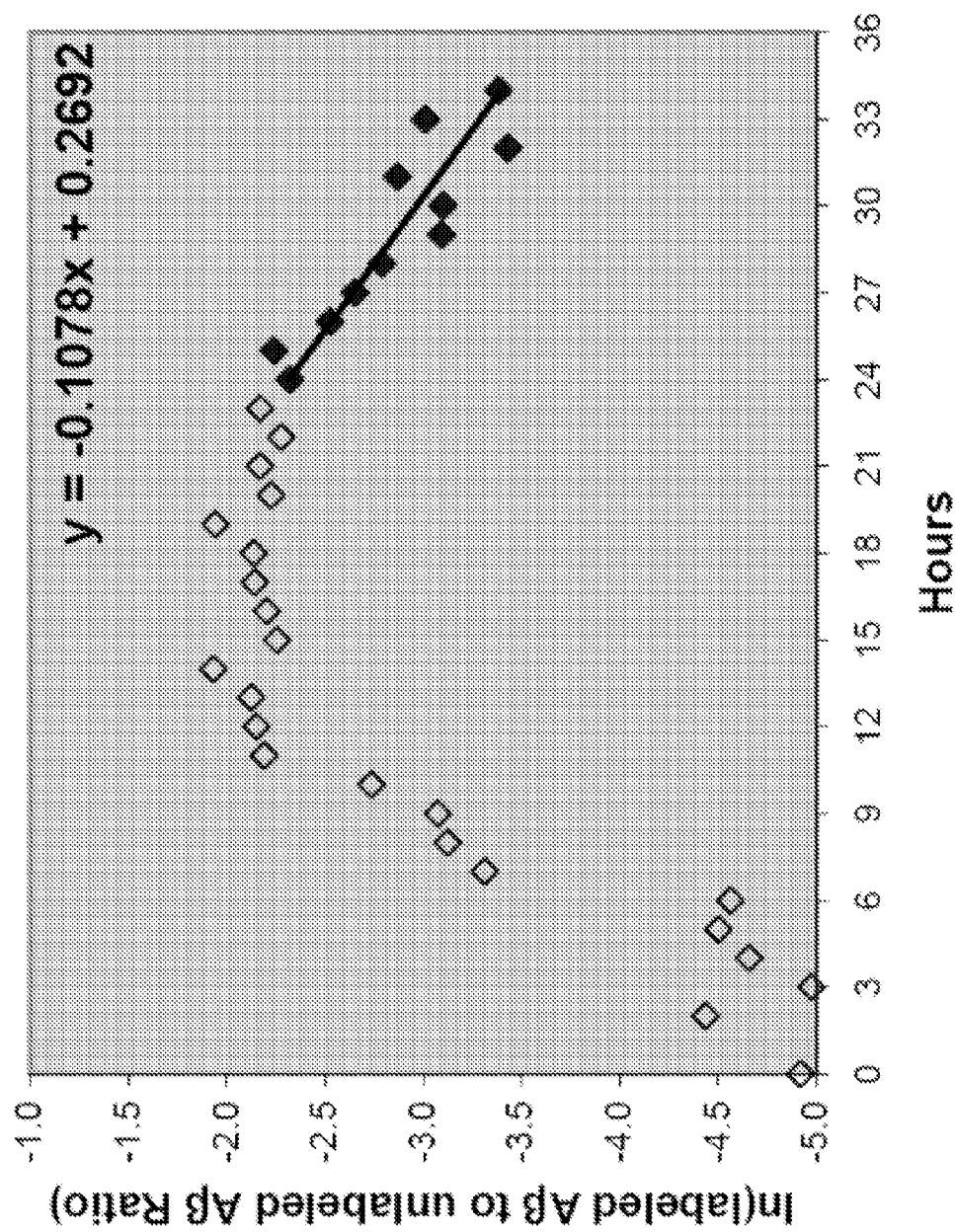
Figure 11F:
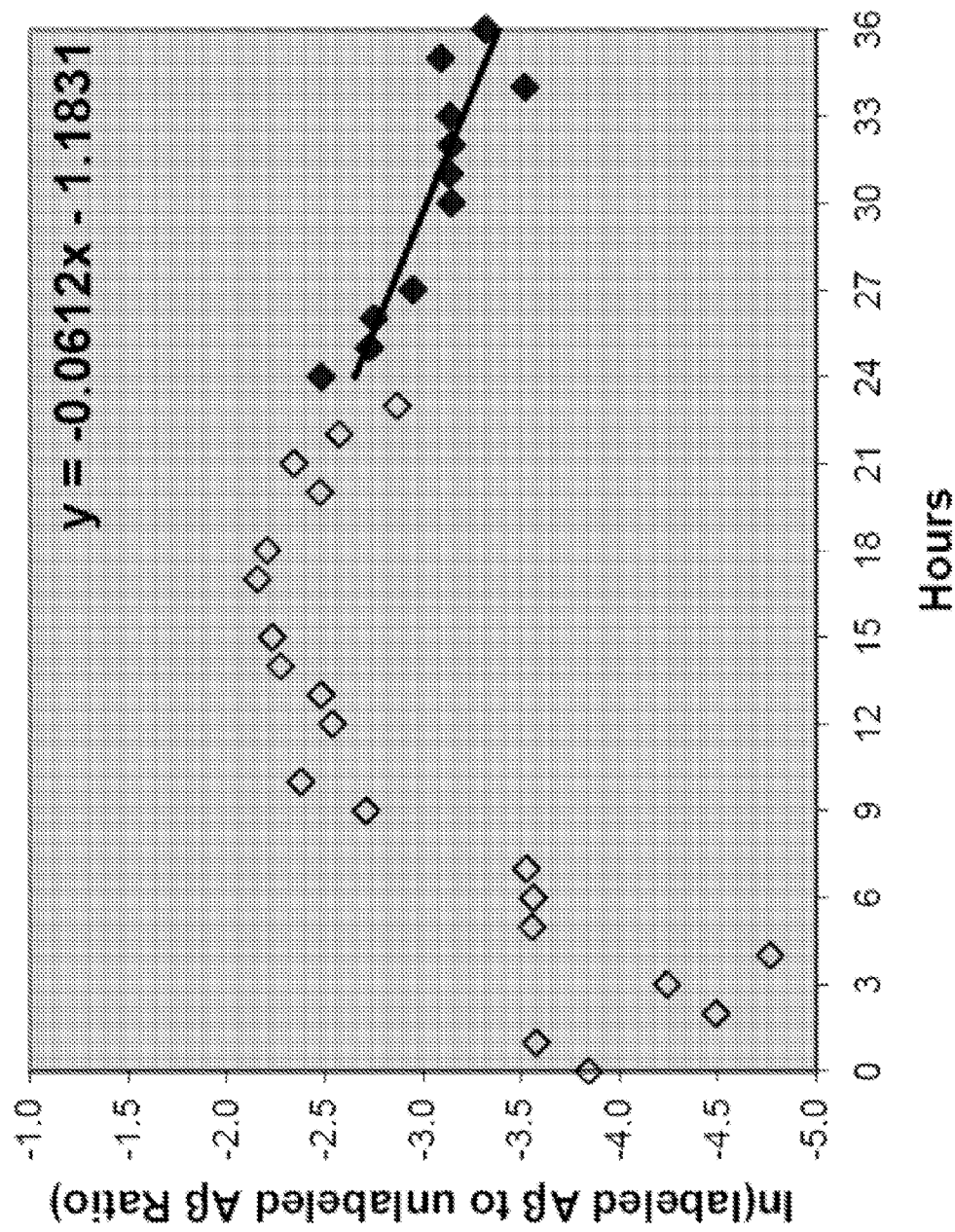
Figure 12:
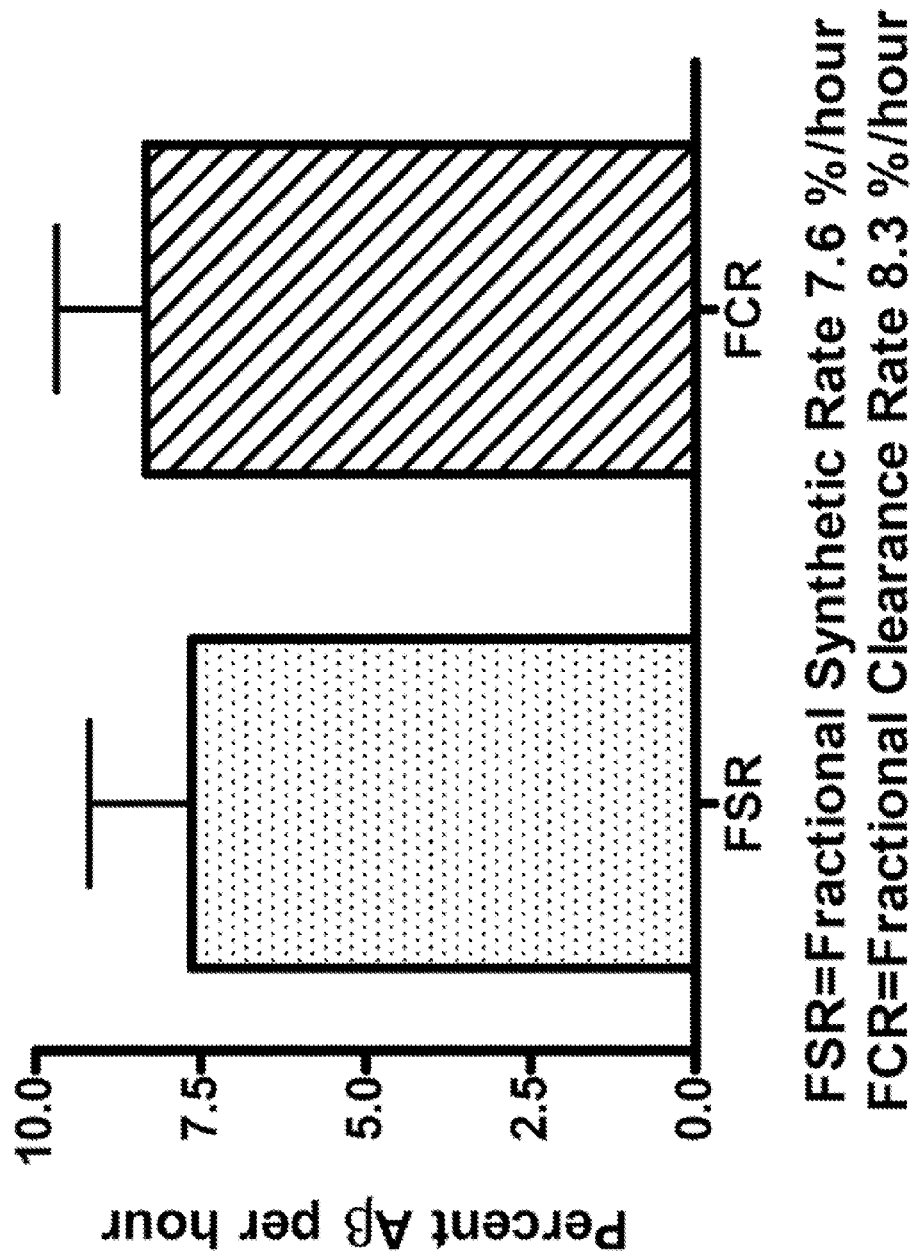
FIG. 12 depicts a graph illustrating the average FSR and FCR. The average Aβ FSR of 6 participants and the average Aβ FCR of 3 participants is shown with standard deviation.

The FCR was operationally defined as the natural log of the labeled Aβ from 24 to 36 hours (FIG. 11D-F). For example, a FCR of 8.3% per hour means that 8.3% of total Aβ was cleared each hour. The average FSR of Aβ for these 6 healthy young participants was 7.6%/hr and the average FCR was 8.3%/hr (FIG. 12). These values were not statistically different from each other.

Example 3

A Technique to Measure Percent Labeled Aβ in Plasma

Rationale

Plasma Aβ metabolism likely occurs in a separate compartment with different metabolism rates compared to CSF. However, a significant amount of plasma Aβ is probably derived from the CNS. In a mouse model of AD, the amount of Aβ captured by an antibody in the plasma, predicted CNS pathology of neurally derived Aβ. Therefore, the metabolism rate of Aβ in plasma may be a defining feature of pathology in AD. In addition, plasma Aβ metabolism may be an equally effective method of measuring Aβ metabolism in humans compared to CSF. If it proves to be diagnostic or predictive of dementia, this method may be more viable as a diagnostic test of pre-clinical or clinical AD.

Experimental Design

As was done for CSF in the prior examples, a method can be developed to measure labeled and unlabeled Aβ in plasma. There are two major differences in obtaining Aβ from plasma compared to CSF: 1) there is ~100× less Aβ in plasma and 2) there is approximately a 200× increase in non-Aβ protein concentration. The efficiency and specificity of the immunoprecipitation may have to be optimized using methods known to one of skill in the art. The immunoprecipitations can be tested by analysis with a Linear Trap Quadrapole (LTQ) mass spectrometer to identify numbers and relative amounts of contaminating proteins. The LTQ provides up to a 200-fold increase in sensitivity over LC-ESI. Preliminary results indicate that it has excellent signal to noise ratio at 50 fold dilution of Aβ fragments from 1 ml of human CSF.

Testing of the optimized methods can be done with 5-10 ml of plasma. Labeled and unlabeled Aβ can by immunoprecipitated, digested with trypsin, and analyzed by mass spectrometry. Labeled plasma samples from subjects can be used to detect and generate plasma labeling standard curves. The sample with the most labeling can be used to create 5 samples by serial dilution. The labeled Aβ can be quantitated by the LTQ in parent ions and tandem mass spectrometry ions, and the results can generate a standard curve. From this curve, the linearity and variability can be determined by a linear fit model. This standard curve can be compared to the standard curve generated for the human CSF Aβ labeling. Labeled plasma Aβ curves can be compared to labeled CSF curves from control versus AD individuals to determine if plasma levels of Aβ can detect or predict AD.

Results

As in data for CSF (see Examples 1 and 2), it is expected that a technique can be developed that can provide reproducible and quantitative measurements of labeled and unlabeled Aβ from human plasma. The standard curves are expected to be near linear and with low variability. It is expected that the plasma labeled Aβ curves from human in vivo studies should closely reflect the CNS/CSF labeled Aβ curves. FSR and FCR of plasma Aβ from participants can also be generated. It is expected that the clearance rates of Aβ in plasma will be much quicker than in the CSF, as has been shown in animal models after Aβ infusion into plasma.

Alternative Approaches

If labeled and unlabeled plasma Aβ cannot be accurately measured as detailed above, then increased sample per time point with fewer time points may be used (20 ml every other hour as opposed to 10 ml every hour). This would decrease temporal resolution of the measurements, but may be still sufficient to generate FSR and FCR. If protein contamination is still be a problem with plasma, then purification by HPLC, protein 2D gel, or even more stringent rinse steps familiar to those of skill in the art may be necessary.

The LTQ is a sensitive mass spectrometer commercially available and provides a very good opportunity to generate measurements based on attomole amounts. There are no better alternatives to this mass spectrometer at present; however, mass spectrometry sensitivity is constantly improving with technology improvements. Those of skill in the art will recognize that the use of such improvements in mass spectrometry is within the scope and spirit of the current invention.

Example 4

Determination of the Effect of ApoE Genotype on CSF Aβ Metabolism

Rationale

ApoE genotype is a well-validated genetic risk factor for AD. Immunohistochemical studies revealed that ApoE co-localized to extracellular amyloid deposits in AD. Furthermore, ApoE ε4 genotype was found to be a risk factor for AD in human populations. The ApoE ε2 allele has been shown to be protective in the risk of AD. ApoE genotype has also been shown to dramatically effect changes in AD pathology in several mouse models of AD (Holtzman et al. 2000 PNAS 97(2892); Fagan eta I. 2002 Neurobiol. Dis 9 (305); Fryer et al. 2005 J Neurosci 25 (2803))

ApoE ε4 dose dependently increases the density of Aβ deposits in AD and in cerebral amyloid angiopathy (CAA). ApoE is associated with soluble Aβ in CSF, plasma and in normal and AD brain. It is likely that ApoE4 is associated with AD and CAA through the common mechanism of influencing Aβ metabolism, although ApoE4 has been shown to be involved in a variety of other pathways.

ApoE isoform has been shown to cause dose and allele dependent changes in time of onset of Aβ deposition and distribution of Aβ deposition in mouse models of AD (Holtzman et al., 2000, Proc. Natl. Acad. Sci. 97: 2892-2897; DeMattos et al. 2004, Neuron 41(2): 193-202). Human ApoE3 was shown to cause a dose dependent decrease in Aβ deposition. In addition, clearance studies have shown that Aβ transport from the CNS to plasma has a $t_{1/2}$ of <30 minutes, which is decreased without ApoE. Together, this suggests that ApoE has Aβ binding and clearance effects on CNS Aβ.

Experimental Design and Analysis

ApoE genotype can be determined in each participant. The Buffy coat (white blood cell layer) from centrifuged plasma can be collected and immediately frozen at −80° C. using standard techniques known to those of skill in the art. The ApoE genotype of the sample is determined by PCR analysis (Talbot et al. 1994, Lancet 343(8910): 1432-1433). The effect of gene dose of ApoE2 (0, 1, or 2 copies) and ApoE4 (0, 1, or 2 copies) can be analyzed with the continuous variable of CSF or plasma FSR or FCR of Aβ metabolism.

Methods for statistical analysis can be made using standard techniques known to those of skill in the art. For example, for the FSR and FCR of Aβ, a two-way or three-way ANOVA can be performed with human ApoE isoform and age as factors in the control group and also in the AD group. If the data are not normally distributed, a transformation can be utilized to meet necessary statistical assumptions regarding Gaussian distributions.

Results

It is expected that ApoE4 can decrease clearance of Aβ compared to ApoE3 in the CNS. Conversely, ApoE2 is expected to increase clearance of Aβ compared to ApoE3 in the CNS. A change in synthesis rate of Aβ based on ApoE genotype is not expected. If changes in Aβ metabolism are detected, this would be evidence of the effect of ApoE status on in vivo Aβ metabolism in humans.

Example 5

Comparison of the ApoE Genotype to Human Plasma Aβ FSR and FCR Metabolism

Rationale

Transport of Aβ from the CNS to plasma may be affected by ApoE genotype, as demonstrated in mouse models of AD. Measurement of this effect in humans may reveal transport changes via ApoE.

In vivo animal data has shown there are different clearance rates of Aβ in plasma vs. CSF vs. brain. The cause of these differences and the relationship between them is not well understood. It is likely that ApoE genotype expression plays a significant role in the transport and clearance of Aβ from the CNS to the CSF and the plasma. ApoE in the CNS is mostly produced by astrocytes and is sialylated and is structurally different compared to plasma Aβ. To better understand the relationship between these compartments as a function of ApoE genotype, the technique from Example 3 can be used to measure the metabolism of Aβ in plasma.

Experimental Design and Analysis

ApoE genotype can be determined in each participant. The Buffy coat (white blood cell layer) from centrifuged plasma can be collected and immediately frozen at −80° C. using standard techniques known to those of skill in the art. The sample can be analyzed using the technique used in Example 4. The effect of gene dose of ApoE2 (0, 1, or 2 copies) and ApoE4 (0, 1, or 2 copies) can be analyzed to the continuous variable of FSR or FCR of plasma Aβ metabolism. Methods for statistical analysis can be made using standard techniques known to those of skill in the art and as described above in Example 4.

Results

It is expected that ApoE4 can decrease the clearance of plasma Aβ compared to ApoE3, and that ApoE2 can increase the clearance of Aβ from the plasma compared to ApoE3. A change in synthesis rate of Aβ based on ApoE genotype is not expected to be observed. If changes in plasma Aβ metabolism are detected, however, this would be the first assessment of the effect of ApoE status on Aβ metabolism in humans.

Alternative Approaches

The relationship between plasma, CSF, and CNS compartments for Aβ metabolism are not well understood. There are changes in the ratios of Aβ in each compartment depending on presence of AD. This indicates a differential effect in the disturbance of Aβ metabolism between compartments. The relationship of peripheral plasma Aβ metabolism compared to CSF Aβ metabolism may be more complex than just ApoE genotype dependent. It is likely that not only AD status, but other factors may interact to effect this relationship. Therefore, a clear pattern of change in Aβ metabolism may not be dependent on ApoE genotype.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

Example 6

Measurement of ApoE Metabolism In Vivo

Rationale

For reasons analogous to those detailed for Example 2, a method for quantifying ApoE FSR and FCR in vivo in the CNS of humans was developed.

Experimental Design and Analysis

Figure 13:
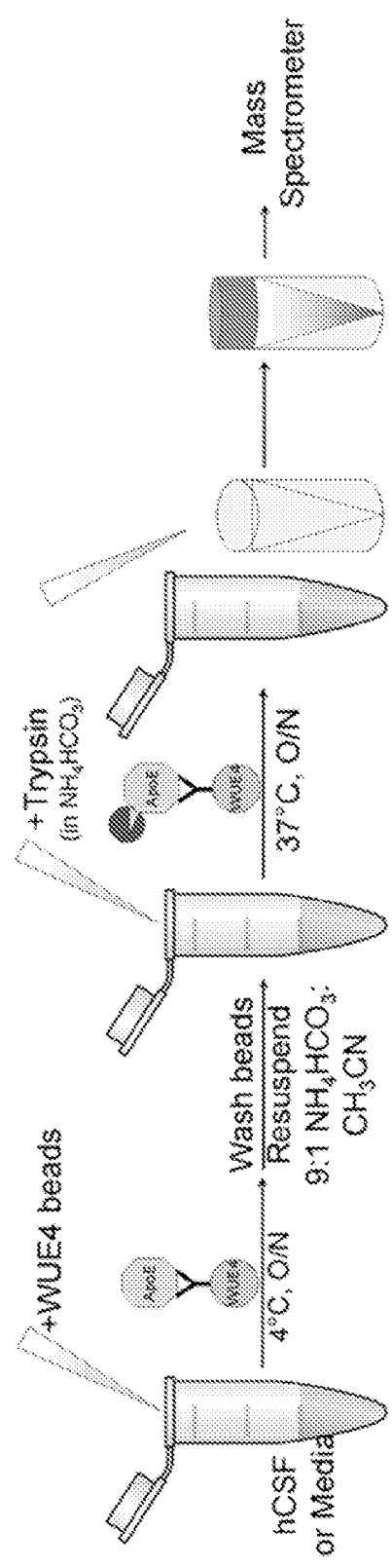
FIG. 13 depicts an illustration of the protocol for quantifying ApoE from human CSF. ApoE from human CSF or astrocyte media is bound to an anti-ApoE antibody (WUE4) coupled to sepharose beads, and digested with trypsin. The supernatant containing ApoE peptides is analyzed by LC-MS.
Figure 14:
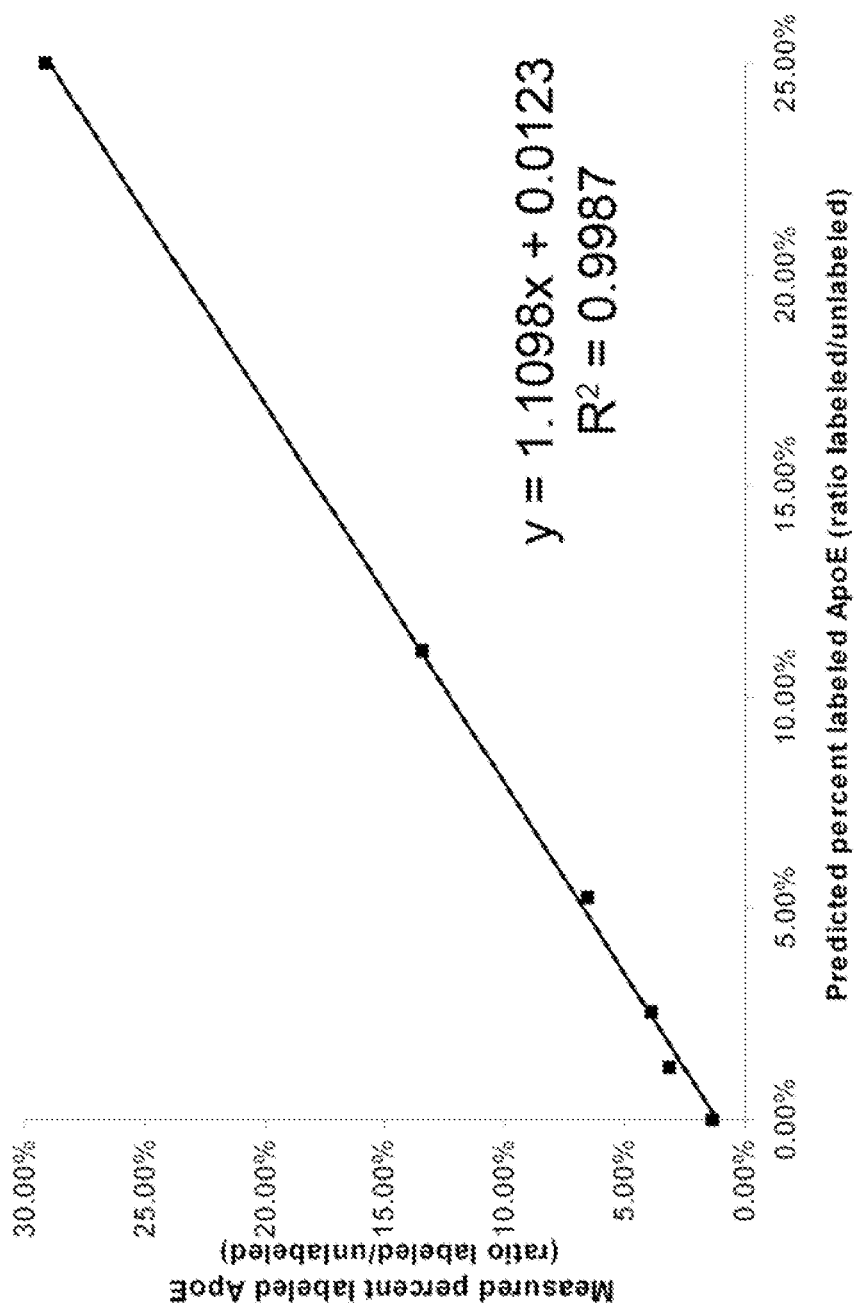
FIG. 14 depicts a graph showing the standard curve of $^{13}C$-Leu-labeled ApoE peptide SWFEPLVEDMQR (SEQ ID NO:3). Stably-transfected mouse astrocytes expressing human ApoE were labeled with $^{13}C_6$-Leu. ApoE was affinity purified from cell media, digested with trypsin, and analyzed by nanoLC tandem MS.

As depicted in FIG. 13, human ApoE was immunoprecipitated from CSF or astrocyte cell culture media using WUE4, a specific anti-human ApoE monoclonal (anti-ApoE) antibody. An immortalized astrocyte cell line from transgenic mice expressing human ApoE was used to produce $^{13}C_6$-labeled leucine ApoE standards. Immunoprecipitated ApoE was then digested with sequencing-grade trypsin. Released peptides were separated by nano liquid chromatography and quantitated by tandem mass spectrometry (nanoLC-MS). The efficiency and selectivity of the immuno-affinity purification was confirmed by analyzing the samples following a general proteomics LC-MS method. Results from Bioworks™3.2, using the SEQUEST algorithm, confirmed ApoE was the predominant protein present in samples, and identified the most abundant peptides containing leucines, which could be used for quantitation. Due to the 6 Da mass shift of a $^{13}C_6$-labeled leucine, unlabeled peptides were distinguishable from labeled peptides. Tandem MS was performed on the peptides of interest, and the percent of $^{13}C$-leucine incorporated into ApoE was determined by calculating the ratio of labeled product ions to unlabeled product ions. A standard curve of $^{13}C_6$-labeled leucine ApoE from cell culture media is shown in FIG. 14. The excellent linearity from 0-25% labeling ($R^2=0.99$) indicates the method developed to measure ApoE is sensitive, specific, and accurate.

Figure 15:
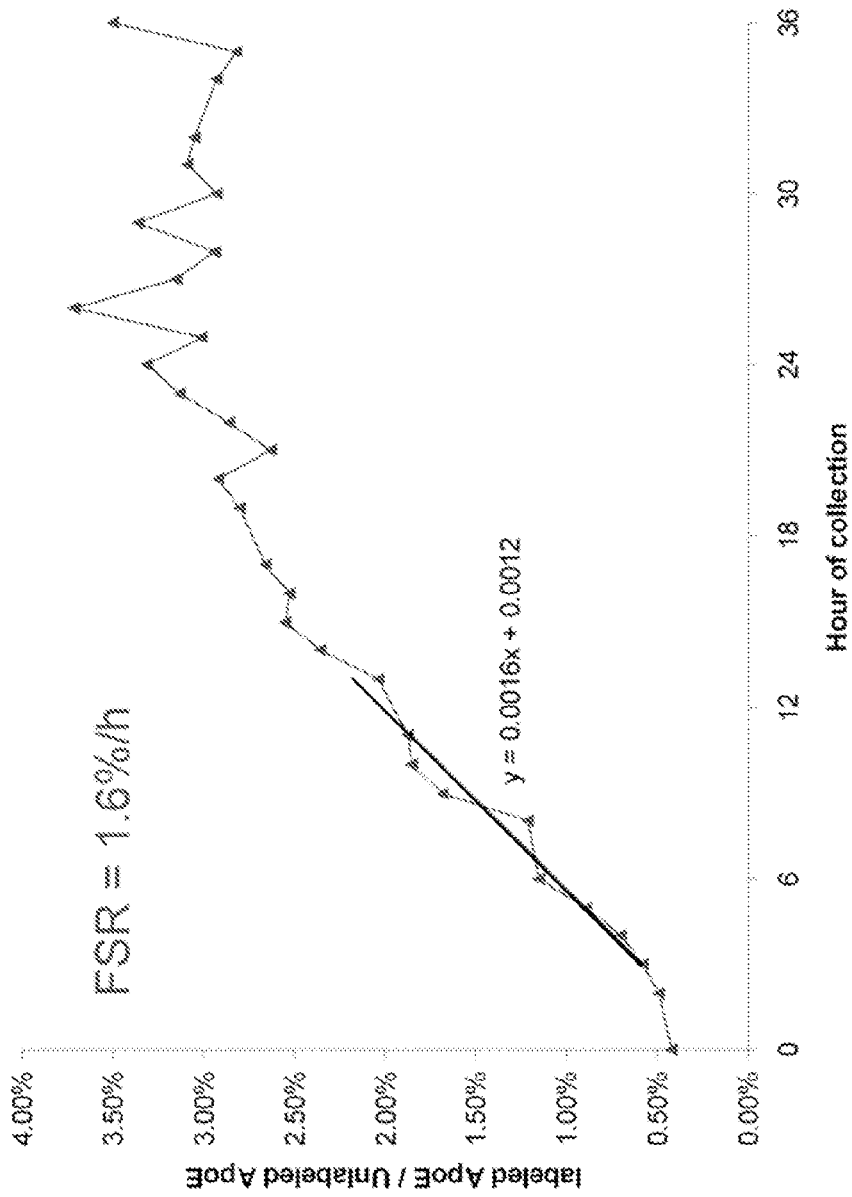
FIG. 15 depicts a graph showing the incorporation of $^{13}C$-Leu into CNS-derived ApoE. ApoE was affinity purified from CSF of a young normal control participant infused with $^{13}C_6$-Leu, and analyzed by nanoLC tandem MS. Fractional synthesis rate (FSR) was calculated using the slope of the linear regression divided by the $^{13}C$-Leu precursor enrichment in CSF ($^{13}C$-Leu=9.86%).
Figure 16:
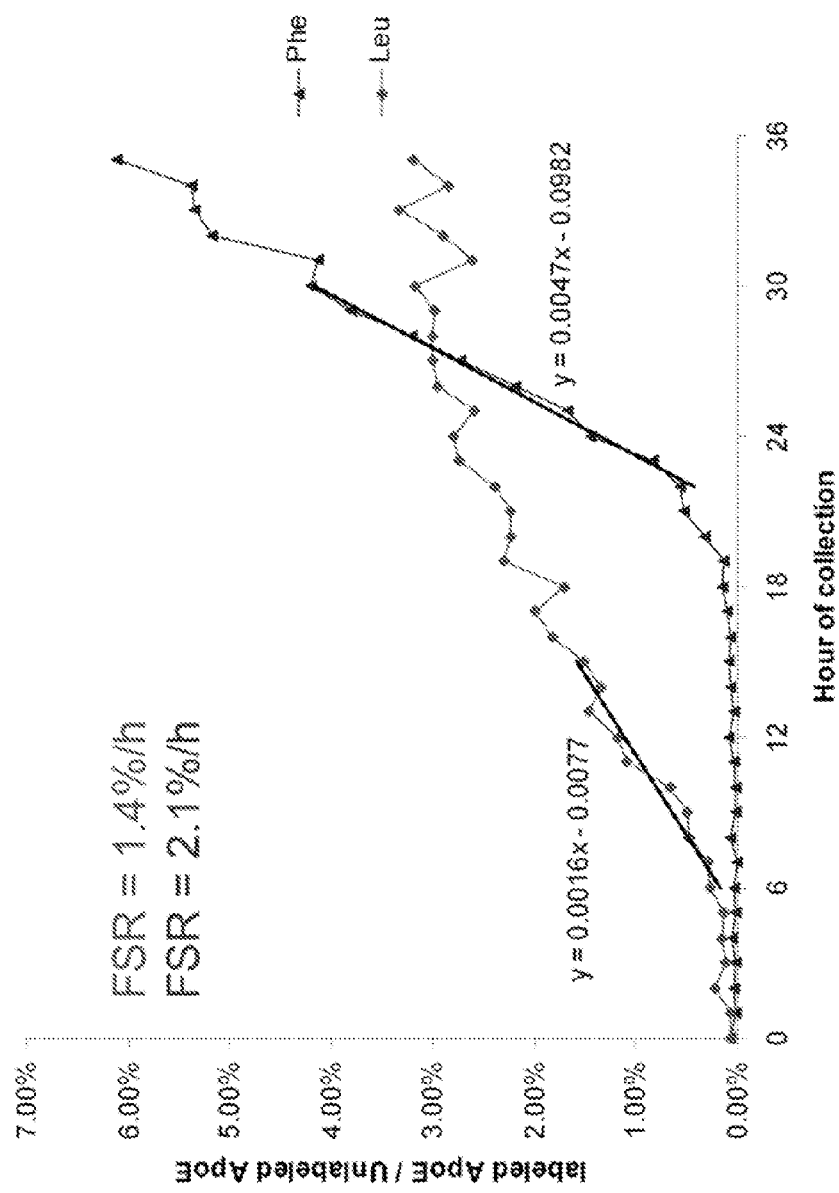
FIG. 16 depicts a graph showing the incorporation of $^{13}C$-Leu and $^{13}C$-Phe into CNS-derived ApoE. ApoE was affinity purified from CSF of a young normal control participant infused with $^{13}C_6$-Leu and $^{13}C_6$-Phe, and analyzed by nanoLC tandem MS. Fractional synthesis rate (FSR) was calculated using the slope of the linear regression divided by the $^{13}C$-Leu or $^{13}C$-Phe precursor enrichment in CSF ($^{13}C_6$-Leu=11.5% or $^{13}C_6$-Phe=22.3%).

In a preliminary experiment, a young normal control participant was infused with $^{13}C_6$-Leucine (Leu) (2 mg/kg/h) from 0-9 hours. CSF was collected every hour for 36 hours. ApoE was affinity purified from CSF, and analyzed by nanoLC-MS. Percent label was calculated from the ratio of the labeled to unlabeled product ions for ApoE tryptic peptide SWFEPLVEDMQR (FIG. 15). Similar results were observed for a young normal control participant infused with $^{13}C_6$-Leu (2 mg/kg/h) from 0-9 hours, followed by infusion with $^{13}C_6$-phenylalanine (Phe) (3 mg/kg/h) from 16-25 hours (FIG. 16). Fractional synthetic rate (FSR) was calculated using the standard formula, dividing the slope of the linear regression by the $^{13}C$-Leu or $^{13}C$-Phe precursor enrichment in CSF. Precursor enrichment for these participants was determined by gas chromatography mass spectrometry (GCMS).

Results

FSR was shown to be approximately 2 percent per hour in these young normal controls (FIG. 15 and FIG. 16). This indicates that approximately half of the ApoE pool is synthesized in the human brain in about 24 hours.

Example 7

Measurement of Soluble Amyloid Precursor Protein Metabolism In Vivo

Rationale

Analogous to the rationale for Examples 2 and 6, a method for quantifying soluble amyloid precursor protein (sAPP) FSR and FCR in vivo in the CNS of humans was developed.

Experimental Design and Analysis

Similar to the method detailed in Examples 2 and 6, sAPP was labeled in the CNS of a human subject. Tandem MS was performed on the peptides of interest, and the percent of $^{13}C_6$-leucine incorporated into sAPP was determined by calculating the ratio of labeled product ions to unlabeled product ions.

Results

Figure 17:
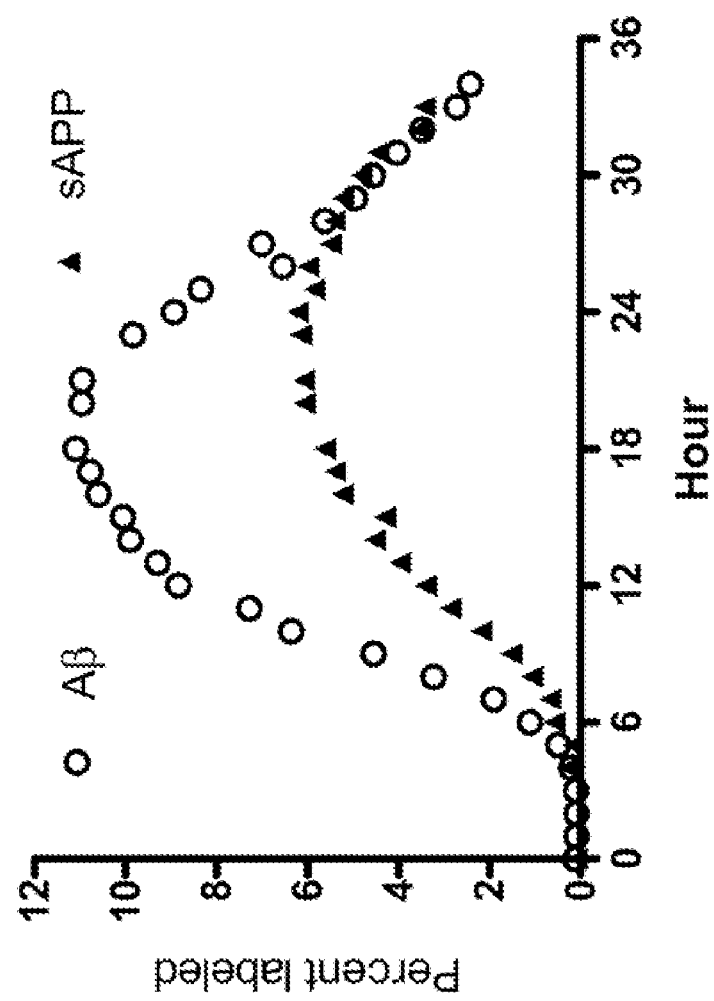
FIG. 17 depicts a graph showing the percent labeled protein over time. Soluble APP has a much slower production and clearance rate compared to Aβ, as indicated by the slower rise in plateau and clearance of labeled sAPP. Open circles =Aβ, Black triangles=soluble amyloid precursor protein (sAPP).

Soluble APP has a much slower production and clearance rate compared to Aβ, as indicated by the slower rise to plateau and clearance of labeled sAPP (FIG. 17). This indicates that individual protein turnover rates are different in the same samples in the same subject.

---

What is claimed is:

1. A method for measuring the in vivo metabolism of a protein in a subject, the protein being synthesized in the central nervous system, the method comprising:
   (a) administering a labeled moiety to the subject, the labeled moiety being capable of crossing the blood brain barrier and incorporating into the protein as the protein is synthesized in the central nervous system of the subject;
   (b) obtaining a biological sample from the subject, the biological sample comprising a protein fraction labeled with the moiety and a protein fraction not labeled with the moiety; and
   (c) detecting the amount of labeled protein and the amount of unlabeled protein by mass spectrometry, wherein the ratio of labeled protein to unlabeled protein is directly proportional to the metabolism of the protein in the subject, wherein the protein is selected from the group consisting of apolipoprotein E, apolipoprotein J, synuclein, soluble amyloid precursor protein, Tau, alpha-2 macroglobulin, S100B, myelin basic protein, an interleukin, and TNF.

2. The method of claim 1, wherein the protein synthesized is from a neuronal cell, glial cell, or other cell in the central nervous system.

3. The method of claim 1, wherein the labeled moiety is an atom, or a molecule with a labeled atom.

4. The method of claim 3, wherein the atom is a radioactive isotope.

5. The method of claim 3, wherein the atom is a non-radioactive isotope.

6. The method of claim 5, wherein the non-radioactive isotope is selected from the group consisting of $^{2}$H, $^{13}$C, $^{15}$N, $^{17}$O, $^{18}$O, $^{33}$S, $^{34}$S, and $^{36}$S.

7. The method of claim 6, wherein the non-radioactive isotope is a component of or attached to an amino acid.

8. The method of claim 7, wherein the amino acid is leucine and the non-radioactive isotope is $^{13}$C.

9. The method of claim 1, wherein the labeled moiety is administered to the subject intravenously, intra-arterially, subcutaneously, intraperitoneally, intramuscularly, or orally.

10. The method of claim 1, wherein the biological sample is cerebral spinal fluid.

11. The method of claim 1, further comprising separating the labeled protein fraction and the unlabeled protein fraction from the biological sample.

12. The method of claim 11, wherein the protein factions are separated by immunoprecipitation.

13. The method of claim 1, wherein the subject is human.

* * * * *

UNITED STATES PATENT AND TRADEMARK OFFICE
CERTIFICATE OF CORRECTION

| | | |
|---|---|---|
| PATENT NO. | : 8,232,107 B2 | Page 1 of 1 |
| APPLICATION NO. | : 13/005233 | |
| DATED | : July 31, 2012 | |
| INVENTOR(S) | : Randall John Bateman et al. | |

It is certified that error appears in the above-identified patent and that said Letters Patent is hereby corrected as shown below:

Col. 24, line 32 (Claim 12, line 1): "factions" should read --fractions--

Signed and Sealed this
Eighteenth Day of September, 2012

David J. Kappos
*Director of the United States Patent and Trademark Office*